United States Patent
Glennon et al.

(10) Patent No.: US 6,806,283 B2
(45) Date of Patent: Oct. 19, 2004

(54) SELECTIVE SEROTONIN RECEPTOR ANTAGONISTS AND THERAPEUTIC APPLICATIONS THEREOF

(75) Inventors: Richard Glennon, Richmond, VA (US); Richard Westkaemper, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 0 days.

(21) Appl. No.: 10/429,970

(22) Filed: May 6, 2003

(65) Prior Publication Data

US 2003/0232872 A1 Dec. 18, 2003

Related U.S. Application Data

(60) Provisional application No. 60/377,606, filed on May 6, 2002, and provisional application No. 60/438,798, filed on Jan. 9, 2003.

(51) Int. Cl.[7] ........................ A61K 31/40; C07D 209/54
(52) U.S. Cl. ........................ 514/409; 514/437; 514/454; 548/411; 549/26; 549/344
(58) Field of Search ................................. 514/409, 454, 514/437; 548/409, 411; 549/26, 344

(56) References Cited

U.S. PATENT DOCUMENTS 3,048,595 A * 8/1962 Zirkle ........................ 546/17

OTHER PUBLICATIONS

Marshall, et al, American Journal of Medical Genetics, 1999, 88:621–627.*

CAS online abstracts Registry No. 7079–91–6, entry date Nov. 16, 1984.*

CAS online abstracts Registry No, 7079–92–7, entry date Nov. 16, 1984.*

* cited by examiner

*Primary Examiner*—Joseph K. McKane
*Assistant Examiner*—Kamal Saeed
(74) *Attorney, Agent, or Firm*—Whitham, Curtis & Christofferson, P.C.

(57) ABSTRACT

Spiro[9,10-dihydroanthracene]-9,3'-pyrrolidine (SPAN) and derivatives thereof are provided as selective serotonin receptor antagonists. The compounds are selective, high affinity antagonists of 5-$HT_2$ serotonin receptors. The compounds are useful as antidepressant and antianxiety agents.

43 Claims, No Drawings

SELECTIVE SEROTONIN RECEPTOR ANTAGONISTS AND THERAPEUTIC APPLICATIONS THEREOF

This application claims the benefit of U.S. provisional applications 60/377,606 and 60/438,798, filed May 6, 2002 Jan. 9, 2003 respectively.

This invention was made using funds from grants from the National Institutes of Health having grant number MH57969. The government may have certain rights in this invention.

BACKGROUND OF THE INVENTION

1. Field of the Invention

The invention generally relates to selective serotonin receptor antagonists and methods of their use as antidepressant and antianxiety agents. In particular, the invention provides spiro[9,10-dihydroanthracene]-9,3'-pyrrolidine (SPAN) and derivatives thereof as selective high affinity antagonists of 5-HT receptors.

2. Background of the Invention

Serotonin (5-hydroxytryptamine, or 5-HT; see Formula 1) is a product of tryptophan metabolism that mediates many diverse physiological activities. Most fundamentally, this well-characterized tryptamine derivative functions as a potent neurotransmitter by regulating G-protein coupled and ligand gated ion channel receptors at the surface of nerve and muscle cells. This activity is mediated by the binding of serotonin to several classes of cell-surface 5-HT receptors. Numerous 5-HT receptors are known and have been categorized into several families (5-HT$_1$–5-HT$_7$) and some are further divided into subfamilies (e.g. 5-HT$_{2A}$ and 5-HT$_{2C}$). Many of the 5-HT receptors have been cloned and their specific functions elucidated.

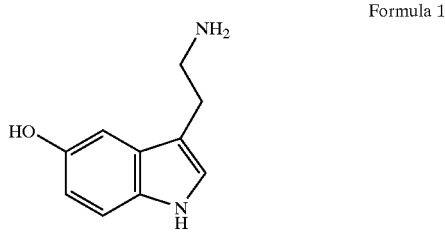

Formula 1

Imbalances in serotonin activity are believed to be responsible for a variety of clinically recognized disorders. For example, many brain disorders in humans are associated with fluctuations in serotonin levels and are effectively treated with drugs that interact specifically with 5-HT receptors or that block the reuptake of serotonin into the presynaptic axon terminals, suggesting that serotonin dysregulation may be involved in these disorders. For example, serotonin receptor ligands are clinically approved as drugs for the treatment of depression, psychosis, anxiety, and certain sexual aberrations, as well as for other conditions such as migraine headaches, chemotherapy-induced nausea, high blood pressure, certain abnormal cardiovascular activities and abnormal thermoregulation.

However, most of these existing agents are relatively nonselective in that they exhibit affinities for several 5-HT receptor classes, as well as for central dopaminergic, noradrenergic, histaminergic, and/or cholinergic receptors, as well as blocking serotonin and dopamine reuptake into the nerve terminus. As a consequence of activity at nonserotonergic sites, the use of these agents may result in undesirable side effects such as tardive dyskinesia, tardive dystonia, excessive weight gain, etc. These side effects can be debilitating and may require clinical treatment in and of themselves. The possibility of the occurrence of side effects is a cause of distress to patients, and is a likely contributor to patient non-compliance with suggested drug therapy regimens.

Ligands which bind with varying degrees or selectivity to some families of 5-HT receptors are known. For example, U.S. Pat. Nos. 5,496,957 and 5,504,101 to Glennon (Mar. 5, 1996 and Apr. 2, 1996, respectively, the complete contents of which are hereby incorporated by reference) describe agents which bind to the 5-HT$_{1D\beta}$ receptor. And U.S. Pat. No. 5,942,536 to Fritz et al. (Aug. 24, 1999, the complete contents of which is hereby incorporated by reference) describes agents which bind to the 5-HT$_{1f}$ receptor. Roth et al. (1994) describe the binding affinities of 36 typical and atypical antipsychotic agents to 5-HT$_6$ and 5-HT$_7$ receptors, and Glennon et al. (1989) describe classes of agents which bind to 5-HT$_{1A}$ receptors. Finally, Glennon et al. (1994) describe the effect of different amine substitutions on phenylalkylamine and indolylalkylamine derivatives which bind to 5-HT$_{2A}$ and 5-HT$_{2C}$ serotonin receptors. There is an ongoing need for the development of alternative agents that selectively bind to specific families of 5-HT receptors with high affinity.

SUMMARY OF THE INVENTION

It is an object of this invention to provide compounds having the formula

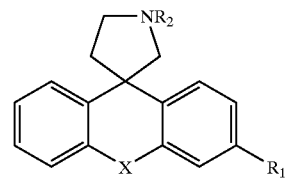

In the compounds, R1 and R2 may be —H, —OH, —OCH$_3$, halogen, aryl, alkylaryl, or substituted or unsubstituted branched or unbranched C$_1$–C$_{10}$ alkyl or alkylaryl, and may be the same or different, and X may be a) carbon with two —H substituents, b) carbon with one or two lower alkyl substituents, or c) a heteroatom or heteroatomic group selected from the group consisting of —O—; —S—; or —SO$_2$—. In some embodiments, R1 may be —H, —CH$_2$CH$_2$CH$_2$Ph, —OCH$_3$, —CH$_2$(CH$_2$)$_4$CH$_3$, phenyl, or —OH. In some embodiments, R2 may be —H, —CH$_3$ or CH$_2$Ph. In some embodiments, X may be —CH$_2$—, —C(CH$_3$)$_2$—, —O— or —S—.

Specific embodiments include compounds with the following formulas:

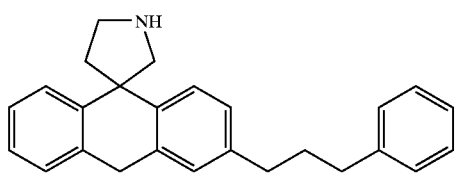

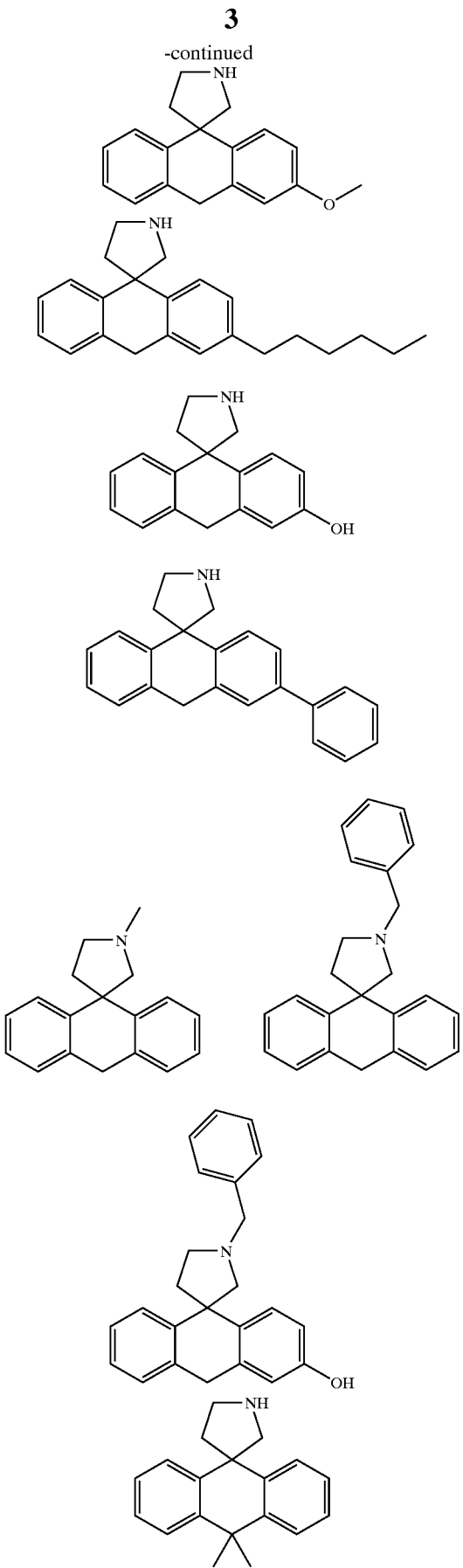

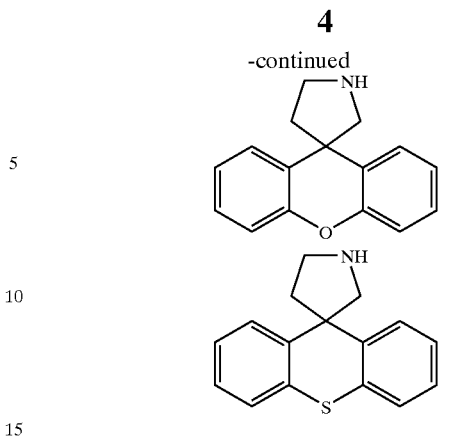

The invention further provides a pharmaceutical composition comprising, a compound of formula

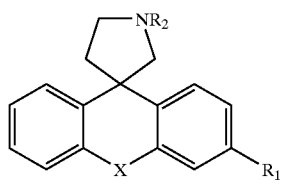

in which R1 and R2 may be —H, —OH, —OCH$_3$, halogen, aryl, alkylaryl, or substituted or unsubstituted branched or unbranched C$_1$–C$_{10}$ alkyl or alkylaryl, and may be the same or different, and X may be a) carbon with two —H substituents, b) carbon with one or two lower alkyl substituents, or c) a heteroatom or heteroatomic group selected from the group consisting of —O—; —S—; or —SO$_2$—. In some embodiments, R1 may be —H, —CH$_2$CH$_2$CH$_2$Ph, —OCH$_3$, —CH$_2$(CH$_2$)$_4$CH$_3$, phenyl, or —OH. In some embodiments, R2 may be —H, —CH$_3$ or CH$_2$Ph. In some embodiments, X may be —CH$_2$—, —C(CH$_3$)$_2$—, —O— or —S—, and a pharmaceutically acceptable carrier.

The present invention also provides a method of treating a condition caused by abnormal serotonin activity in a patient in need thereof. The method includes the step of administering a compound of formula

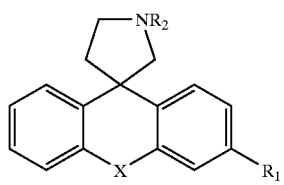

in which R1 and R2 may be —H, —OH, —OCH$_3$, halogen, aryl, alkylaryl, or substituted or unsubstituted branched or unbranched C$_1$–C$_{10}$ alkyl or alkylaryl, and may be the same or different, and X may be a) carbon with two —H substituents, b) carbon with one or two lower alkyl substituents, or c) a heteroatom or heteroatomic group selected from the group consisting of —O—; —S—; or —SO$_2$—. In some embodiments, R1 may be —H, —CH$_2$CH$_2$CH$_2$Ph, —OCH$_3$, —CH$_2$(CH$_2$)$_4$CH$_3$, phenyl, or —OH. In some embodiments, R2 may be —H, —CH$_3$ or CH$_2$Ph. In some embodiments, X may be —CH$_2$—, —C(CH$_3$)$_2$—, —O— or —S—. The compound is administered in a quantity sufficient to ameliorate symptoms of said condition in said patient. The condition may be for example, clinical depression or anxiety, schizophrenia, schizoaffective disorder, and various eating and sleeping disorders. The compound may be an antagonist of 5HT2 receptors, an antagonist of H1 receptors, or an antagonist of both 5HT2 receptors and H1 receptors.

The invention further provides a method of blocking a 5HT2 receptor in a patient in need thereof. The method includes the step of administering to the patient of a compound of formula

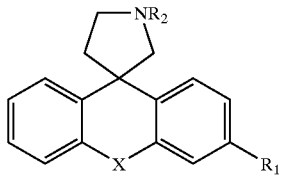

in which R1 and R2 may be —H, —OH, —OCH$_3$, halogen, aryl, alkylaryl, or substituted or unsubstituted branched or unbranched $C_1$–$C_{10}$ alkyl or alkylaryl, and may be the same or different, and X may be a) carbon with two —H substituents, b) carbon with one or two lower alkyl substituents, or c) a heteroatom or heteroatomic group selected from the group consisting of —O—; —S—; or —SO$_2$—. In some embodiments, R1 may be —H, —CH$_2$CH$_2$CH$_2$Ph, —OCH$_3$, —CH$_2$(CH$_2$)$_4$CH$_3$, phenyl, or —OH. In some embodiments, R2 may be —H, —CH$_3$ or CH$_2$Ph. In some embodiments, X may be —CH$_2$—, —C(CH$_3$)$_2$—, —O— or —S—. The compound is administered in a quantity sufficient to block the 5HT2 receptor.

The invention further provides a method of blocking an H1 receptor in a patient in need thereof The method includes the step of administering to the patient a compound of formula

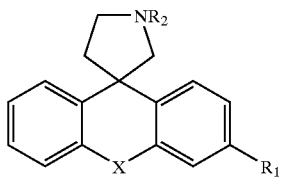

in which R1 and R2 may be —H, —OH, —OCH$_3$, halogen, aryl, alkylaryl, or substituted or unsubstituted branched or unbranched $C_1$–$C_{10}$ alkyl or alkylaryl, and may be the same or different, and X may be a) carbon with two —H substituents, b) carbon with one or two lower alkyl substituents, or c) a heteroatom or heteroatomic group selected from the group consisting of —O—; —S—; or —SO$_2$—. In some embodiments, R1 may be —H, —CH$_2$CH$_2$CH$_2$Ph, —OCH$_3$, —CH$_2$(CH$_2$)$_4$CH$_3$, phenyl, or —OH. In some embodiments, R2 may be —H, —CH$_3$ or CH$_2$Ph. In some embodiments, X may be —CH$_2$—, —C(CH$_3$)$_2$—, —O— or —S—. The compound is administered in a quantity sufficient to block the H1 receptor.

The invention further provides a method of blocking both a 5HT2 receptor and an H1 receptor in a patient in need thereof. The method includes the step of administering to the patient a compound of formula

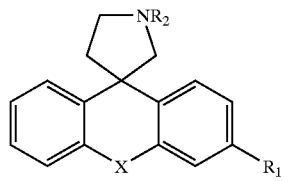

in which R1 and R2 may be —H, —OH, —OCH$_3$, halogen, aryl, alkylaryl, or substituted or unsubstituted branched or unbranched $C_1$–$C_{10}$ alkyl or alkylaryl, and may be the same or different, and X may be a) carbon with two —H substituents, b) carbon with one or two lower alkyl substituents, or c) a heteroatom or heteroatomic group selected from the group consisting of —O—; —S—; or —SO$_2$—. In some embodiments, R1 may be —H, —CH$_2$CH$_2$CH$_2$Ph, —OCH$_3$, —CH$_2$(CH$_2$)$_4$CH$_3$, phenyl, or —OH. In some embodiments, R2 may be —H, —CH$_3$ or CH$_2$Ph. In some embodiments, X may be —CH$_2$—, —C(CH$_3$)$_2$—, —O— or —S—. The compound is administered in a quantity sufficient to block both the 5HT2 and the H1 receptor.

DETAILED DESCRIPTION OF THE PREFERRED EMBODIMENTS OF THE INVENTION

The present invention provides certain compounds that exhibit high binding affinity for serotonin receptors 5-HT$_{2A}$ and 5-HT$_{2C}$. Without being bound by theory, the compounds appear to act as antagonists of these receptors. By "antagonist" we mean the compounds block the action of endogenous serotonin at the receptor and prevent activation of the receptor.

Further, the compounds of the present invention are highly selective, being essentially devoid of affinity for the dopamine D2 receptors and the serotonin and norepinephrine transporters. As such, the compounds are useful for treating conditions for which it is desirable to selectively block serotonin receptor function with an antagonist. Because the compounds are highly selective for the target receptors, they cause fewer side effects than previously known serotonin receptor ligands.

A generic chemical structure of the compounds of the present invention is given in Formula 2.

Formula 2

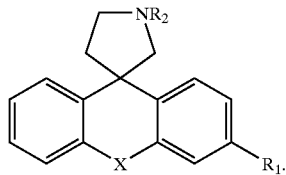

In Formula 2:

R1 and R2 may be —H, —OH, —OCH$_3$, halogen, aryl, alkylaryl, or substituted or unsubstituted branched or unbranched $C_1$–$C_{10}$ alkyl or alkylaryl, and may be the same or different. X may be a) carbon with two —H substituents, b) carbon with one or two lower alkyl substituents, or c) a heteroatom or heteroatomic group, examples of which include but are not limited to —O—, —S—, and —SO$_2$—.

By "alkylaryl" we mean an aryl substituted with a $C_1$–$C_4$ alkyl, or a $C_1$–$C_{10}$ alkyl bridging between an aryl substituent (e.g. phenyl) and the phenyl moiety depicted in Formula 2.

"Phenyl" and "benzyl" are used interchangably herein. Lower alkyl substituents include branched or unbranched $C_1$–$C_4$ alkyl groups such as methyl, ethyl, etc. Branched or unbranched $C_1$–$C_{10}$ alkyl or alkylaryl may be substituted, i.e. one or more of the hydrogens may be replaced with a non-hydrogen atom or chemical group, for example, with other alkyl groups such as lower alkyls, phenyl, etc.

Exemplary substituents $R_1$, $R_2$ and X of generic Formula 2 are as given in Table 1 where "Compound Number" refers to the number assigned to the compound in the synthesis schemes described in the Examples section.

TABLE 1

Examples of $R_1$, $R_2$ and X Substituents

| Compound Number | $R_1$ | $R_2$ | X |
|---|---|---|---|
| [5] | —H | —H | —$CH_2$— |
| [23] | —$CH_2CH_2CH_2Ph$ | —H | —$CH_2$— |
| [17] | —$OCH_3$ | —H | —$CH_2$— |
| [21] | —$CH_2(CH_2)_4CH_3$ | —H | —$CH_2$— |
| [17a] | —OH | —H | —$CH_2$— |
| [25] | —Ph | —H | —$CH_2$— |
| [6] | —H | —$CH_3$ | —$CH_2$— |
| [7] | —H | —$CH_2Ph$ | —$CH_2$— |
| [22] | —$CH_2CH_2CH_2Ph$ | —$CH_2Ph$ | —$CH_2$— |
| [16] | —$OCH_3$ | —$CH_2Ph$ | —$CH_2$— |
| [20] | —$CH_2(CH_2)_4CH_3$ | —$CH_2Ph$ | —$CH_2$— |
| [18] | —OH | —$CH_2Ph$ | —$CH_2$— |
| [12] | —H | —H | —$C(CH_3)_2$— |
| [30] | —H | —H | —O— |
| [36] | —H | —H | —S— |

The simplest "least substituted" compound of the present invention is spiro[9,10-dihydroanthracene]-9,3'-pyrrolidine [5] (SPAN), the formula for which is given in Formula 3.

Formula 3

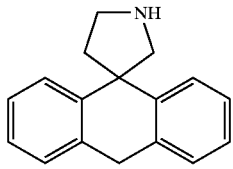

In compound [5], the synthesis of which is described in Example 1, $R_1$ and $R_2$ are both —H and X is —$CH_2$—. The other compounds of the invention are generally substituted with more complex chemical groups (i.e. with chemical groups composed of more atoms) and thus may be considered as derivatives or analogs of [5]. By "derivatives" or "analogs" we mean that the other compounds of the invention have the basic chemical structure of compound [5] but contain different chemical groups at one or more of positions $R_1$, $R_2$ and X.

The compounds of the present invention are ligands of (i.e. bind to) serotonin receptors 5-$HT_2$ and 5-$HT_{2A}$ and 5-$HT_{2C}$. By "high affinity" we mean that the compounds display a Ki in the range of about less than 1 to about 500 nM. In contrast, compounds with low or moderate affinities diplay Ki values in the range of about 2000 to about 10,000 nM, and about 500 to about 2000 nM, respectively. For example, compound [5] displays a Ki of 4nM for 5-$HT_2$ receptors and a Ki of 24 nM for the structurally related 5-$HT_{2c}$ receptor and is therefore a high affinity ligand for both receptors.

In addition, the compounds of the present invention are selective for 5$HT_2$ serotonin receptors 5-$HT_2$, 5-$HT_{2A}$ and 5-$HT_{2C}$. By "selective" we mean that the affinity of the compounds for serotonin receptors is significantly higher than for other related receptor types. For example, a compound with low selectivity typically has an affinity of about 10-fold or less higher than for other related receptor types, whereas moderately and highly selective compounds display about 10–100 fold and about 100 to 10,000 fold higher affinities, respectively. By "related receptor types" we mean other receptors implicated in the most serous side effects of typical 5$HT_2$ antagonists, e.g. the D2 receptor, and the serotonin and norepinephrine transporters. For example, compound [5] displays a Ki of 4 nM for the 5-$HT_2$ receptor and a Ki of 24 nM for the structurally related 5-$HT_{2c}$ receptor but is essentially devoid of binding activity for the dopamine D2 receptor (Ki=5040 nM), the serotonin transporter (Ki>10,000 nM) and the norepinephrine transporter (Ki>10,000 nM).

The compounds of the present invention are useful in treating a variety of disorders that result from abnormal serotonin activity. They may be used as prophylactic and/or acute-phase remedies for the relief and reversal of serotonin-regulated symptoms. In particular, disorders that result from an increased synaptic concentration of serotonin, in particular as found in depressive disorders, and that can be ameliorated by inhibition of the 5$HT_2$ serotonin receptors. Examples of such conditions include but are not limited to clinical depression or anxiety, schizophrenia, schizoaffective disorder, and various eating and sleeping disorders.

The present invention also encompasses a pharmaceutical preparation comprising at least one compound of the present invention together with a pharmaceutically acceptable carrier. The compounds of the invention can be used either as the free base or as the pharmaceutically acceptable acid-addition salt form, for example, hydrochloride, hydrobromide, tartrate, and maleate. Such a pharmaceutical preparation may be in any of many forms suitable for administration of drugs, including but not limited to injectable dosage forms and solid dosage forms such as tablets, capsules, and the like. The compounds can be administered in the pure form or in a pharmaceutically acceptable formulation including suitable elixirs, binders, and the like, or as pharmaceutically acceptable salts or other derivatives. It should be understood that the pharmaceutically acceptable formulations and salts include liquid and solid materials conventionally utilized to prepare injectable dosage forms and solid dosage forms such as tablets and capsules. Water may be used for the preparation of injectable compositions which may also include conventional buffers and agents to render the injectable composition isotonic. Other potential additives include: colorants; surfactants (TWEEN, oleic acid, etc.); and binders or encapsulants (lactose, liposomes, etc). Solid diluents and excipients include lactose, starch, conventional disintergrating agents, coatings and the like. Preservatives such as methyl paraben or benzalkonium chloride may also be used. Depending on the formulation, it is expected that the active composition will consist of 1–99% of the composition and the vehicular "carrier" will constitute 1–99% of the composition. The pharmaceutical compositions of the present invention may include any suitable pharmaceutically acceptable additives or adjuncts to the extent that they do not hinder or interfere with the therapeutic effect desired of agent.

The invention further provides a method for treating clinical disorders resulting from aberrant serotonin activity in a patient in need of such treatment. According to the method, at least one compound of the present invention is administered to the patient in a quantity sufficient to ameliorate symptoms of such disorders.

Those of skill in the art will recognize that the exact dosage of an agent to be so-administered may vary depending on factors such as the age, gender, weight and overall health status of the individual patient, as well as on the nature of the disorder being treated. Generally, dosages in the range of from about 0.1 to about 1000 mg active agent/kg body weight/24 hr., and more preferably about 1.0 to about 500.0 mg active agent/kg body weight/24 hr., and even more preferably about 10 to about 100.0 mg active agent/kg body weight/24 hr., are effective. The level of efficacy and optimal amount of dosage for any given compound may vary from compound to compound.

The agents of the present invention may be administered by any of a wide variety of means which are well known to those of skill in the art, (including but not limited to intravenously, intramuscularly, intraperitoneallly, orally, rectally, intraocularly, and the like) or by other routes (e.g. transdermal, sublingual, aerosol, etc.). and may be in any form (e.g. liquid, solid, etc.) which is suitable for the means of administration. Further, the agents may be administered either alone or together with other medications in a treatment protocol.

Further, several of the compounds (e.g. [5], [16], [17], [30] and [36] of the present invention also display a high affinity for the histamine H1 receptor, high affinity being defined herein as displaying a Ki value of about 100 nm or less. This receptor is known to function in allergic reactions in the periphery and regulation of sleep in the central nervous system. Thus, compounds of the present invention may also be utilized to treat conditions in which it is desirable to antagonize the action of histamine at Hi receptors. Examples of such conditions include but are not limited to sleep disorders and allergic reactions.

Finally, the compounds of the present invention may be used as above for determining 5-HT$_2$ receptor family function, for example, in a laboratory or clinical diagnostic setting.

EXAMPLES

Example 1

Synthesis of Spiro[9,10-dihydroanthracene-]9,3'-pyrrolidine [5] (SPAN)

The synthesis of SPAN was carried out as depicted in Scheme 1 and as further described below. Referring to Scheme 1, reagents and conditions were as follows: (a) POCl$_3$, reflux, 45 min, (b) C$_2$H$_5$ONa, BrCH$_2$COOC$_2$H$_5$, EtOH, reflux, (c) 10% Pd/C, CH$_3$OH, HCl, (d) Borane-THF/THF; 6.0M HCl.

Scheme 1

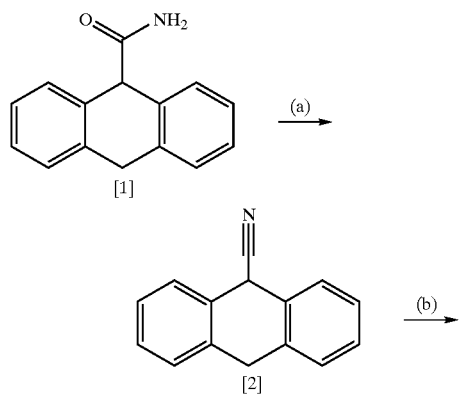

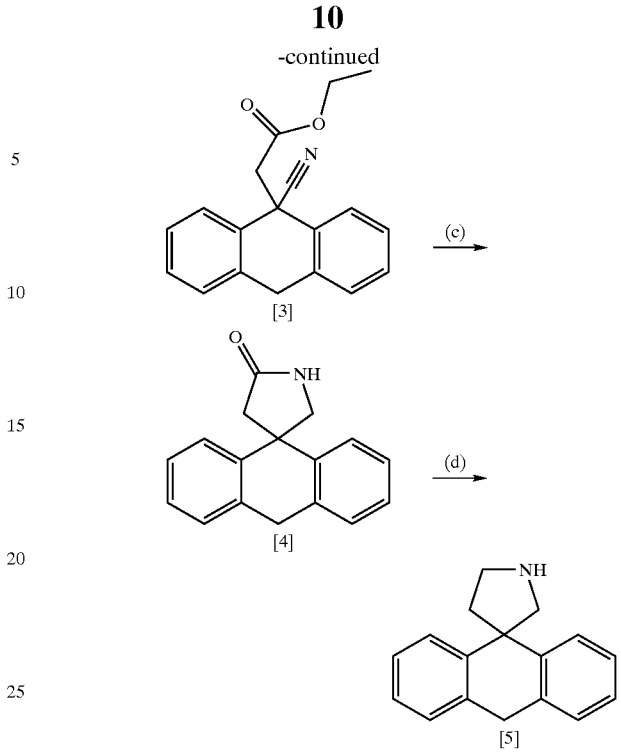

9-Cyano-9,10-dihydroanthracene [2]

POCl$_3$ (5.5 mL, 59 mmol) was added to crystalline 9,10-dihydroanthracene carboxamide [1] (0.54 g, 2.43 mmol) while stirring. The solution was then heated at reflux (45 min), when TLC showed complete absence of starting material. The solution was then poured into a mixture of crushed ice and NH$_4$OH with vigorous stirring. The solution was stirred (15 min) and excess of NH$_4$OH was added to keep the solution alkaline. The solid formed was extracted with ether (3×50 ml). The combined ether extracts were washed with water and brine, dried (MgSO$_4$) and evaporated under reduced pressure to give an yellow oil which crystallized immediately. The product was purified by mplc using pet. ether: acetone (9:1) as eluent to give 0.296 g (60%) of pure 9-Cyano-9,10-dihydroanthracene as colorless crystals mp. 106–108° C. **lit. mp. 101–102° C. IR$^{cm-1}$ 2215. $^1$H NMR (CDCl$_3$)d: 3.87–3.93 (d, J=18 Hz, 1H, CH$_2$), 4.05–4.11 (d, J=18 Hz, 1H, CH$_2$), 5.02 (s, 1H, CH), 7.28–7.79 (m, 8H, Ar—H). $^{13}$C NMR (CDCl$_3$) d: 36.14, 37.60, 119.54, 125.88, 127.12, 127.60, 128.53, 128.82, 129.56, 131.34, 136.65

(9-Cyano-9,10-dihydro-anthracen-9-yl)-acetic acid ethyl ester [3]

9-Cyano-9,10-dihydroanthracene [2] (1.25 g, 6.09 mmol) was added to sodium ethoxide prepared from Na (0.196 g, 8.53 mmol) and EtOH (10 mL) and heated at reflux (1 hr). The solution was then cooled in an ice bath and ethyl bromoacetate (1.42 g, 8.53 mmol) was added drop wise via a syringe. The resulting mixture was heated at reflux (4 h) cooled and filtered. The residue was washed with ether (25 mL). Water (25 mL) was added to the filtrate and the organic layer was separated. The aqueous layer was once again extracted with ether (25 mL). The combined ether extracts were washed with water and brine, dried (MgSO$_4$) and evaporated under reduced pressure to give an oil which was purified by mplc using pet. ether: EtOAc (9:1) as eluent to give 1.245 g (70%) of the product as a colorless oil, which crystallized on prolonged standing: mp 69–70° C. (EtOAc-pet. ether). $^1$H NMR (CDCl$_3$)d: 1.10–1.15 (t, J=7.5 Hz, CH$_3$), 2.85 (s, 2H, CH$_2$), 3.97–4.14 (m, 4H, CH$_2$), 7.33–7.89 (m, 8H, Ar—H). $^{13}$C NMR (CDCl$_3$)d: 14.53, 35.27, 46.05, 46.28, 61.63, 121.89, 127.58, 127.70, 128.93, 134.21, 135.10, 167.96

Spiro [9,10-dihydroanthracene]-9,4'-pyrrolidin-2'-one [4]

A mixture of (9-Cyano-9,10-dihydro-anthracen-9-yl)-acetic acid ethyl ester [3] (0.60 g, 2.061 mol), 10% Pd/C (0.15 g) in methanol (40 mL) and HCl (1 mL) was hydrogenated at 50 kg/cm$^3$ (3 days). The catalyst was filtered off with celite and the solvent was evaporated under reduced pressure to give a white semisolid. Water (25 mL) was added and the solution was made basic with 10% NaOH and extracted with EtOAc (3×25 mL). The combined EtOAc extracts were washed with water and brine, dried (MgSO$_4$) and evaporated under reduced pressure to give a colorless oil which crystallized immediately on standing. The solid was recrystallized from CHCl$_3$-pet.ether to give 0.35 g (68%) of the pure amide as a white crystalline solid: mp 189–190° C. $^1$H NMR (CDCl$_3$)d: 3.06 (s, 2H, CH$_2$), 3.70 (s, 2H, CH$_2$), 4.00–4.06 (d, J=18 Hz, 1H, CH$_2$), 4.09–4.15 (d, J=18 Hz, 1H, CH$_2$), 6.15 (s, 1H, NH), 7.24–7.58 (m, 8H, Ar—H). $^{13}$C NMR (CDCl$_3$)d: 36.37, 43.20, 47.49, 55.66, 125.04, 127.50, 128.73, 136.35, 141.36, 178.40

Spiro[9,10-dihydroanthracene]-9,3'-pyrrolidine [5]

A 1.0 M solution of BH$_3$-THF complex (7.00 ml, 7.00 mmol) was added at 0° C. to a well stirred solution of 4-Spiro-9-(9,10-dihydroanthracene)pyrrolidin-2-one [4] (0.35 g, 1.40 mmol) in anhydrous THF (2 mL). The solution was brought to RT and then heated at reflux (8 h), cooled to RT and 6 M solution of HCl (4 mL) was added cautiously to the reaction mixture. The reaction mixture was then heated at reflux (1 hr), cooled to RT and the solvent was removed under reduced pressure, resulting in a white suspension. Water (20 mL) was added to it and extracted with EtOAc (20 mL). The aqueous phase was then basified using 10% NaOH and extracted with Et$_2$O (3×25 ml). The combined Et$_2$O extracts were washed with water and brine, dried (MgSO$_4$) and the solvent was removed under reduced pressure to give 0.31 g (94%) the amine as colorless oil. The oil started to darken rapidly and was dissolved in anhydrous acetone and fumaric acid (0.15 g, 1.31 mmol) was added and heated. The solution on cooling gave the fumarate as pale pink powder, which remained on two recrystallizations. mp. 190.5–191.5° C. (EtOAc—CH$_3$OH). $^1$H NMR (DMSO-d$_6$) d: 2.25–2.30 (t, J=7.5 Hz, 2H, CH$_2$), 3.21–3.26 (t, J=7.5 Hz, 2H, CH$_2$), 3.55 (s, 2H, CH$_2$), 4.06 (s, 2H, CH$_2$), 6.44 (s, 1H, fumarate), 7.20–7.56 (m, 8H, Ar—H). $^{13}$C NMR (DMSO-d$_6$)d: 36.22, 36.67, 45.18, 51.09, 54.10, 124.43, 126.69, 126.76, 128.17, 135.84, 137.08, 141.44, 168.96. Anal. Calcd. For (C$_{17}$H$_{17}$N.½C$_4$H$_4$O$_4$): C, 77.79; H, 6.52; N, 4.77. Found. C, 77.12; H, 6.56; N, 4.78

Example 2

Synthesis of Spiro[9,10-dihydroanthracene]-9,3'-(1-methyl)-pyrrolidine [6]

The synthesis of compound [6] was carried out as depicted in Scheme 2 and as described below. Referring to Scheme 2, reagents and conditions were as follows: (a) NaCNBH$_3$/CH$_3$CN.

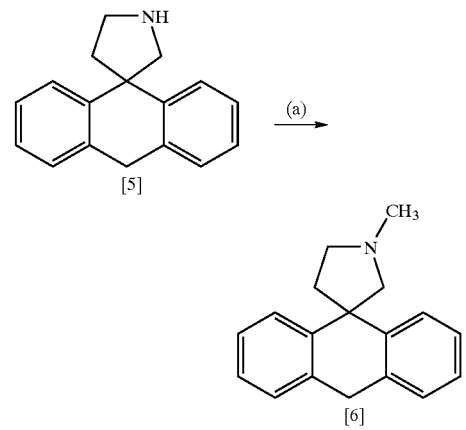

Scheme 2

Spiro[9,10-dihydroanthracene]-9,3'-pyrrolidine [5] (0.23 g, 1.0 mmol) was dissolved in a mixture of anhydrous CH$_3$CN (10 mL) and formaldehyde (37%, 0.5 mL). NaCNBH$_3$ (0.10 g, 1.6 mmol) was added in portions over 5 min. and the reaction mixture was stirred (45 min) at room temperature. Glacial acetic acid was added dropwise until the solution tested neutral. Stirring was continued for another 45 min, glacial acetic acid being added occasionally to maintain pH. The solvent was removed under reduced pressure and 2 N NaOH (20 mL) was added and extracted with Et$_2$O (2×25 mL). The combined Et$_2$O extracts were then extracted with 1N HCl (3×25 mL). The acid extracts were combined and neutralized with solid NaOH and extracted with Et$_2$O (3×25 mL). The combined Et$_2$O extracts were washed with water, brine, dried (MgSO$_4$) and evaporated under reduced pressure to give 0.155 g (63%) of colorless oil. The oil was dissolved in anhydrous acetone and fumaric acid (0.079 g, 0.68 mmol) was added and heated to dissolve the acid. The solution on cooling the product as a white powder: mp. 162–163° C. (EtOAc—CH$_3$OH). $^1$H NMR (DMSO-d$_6$)δ: 2.39–2.44 (t, J=7.5 Hz, 2H, CH$_2$), 2.46 (s, 3H, CH$_3$), 3.00–3.04 (t, J=6 Hz, 2H, CH$_2$), 3.11 (s, 2H, CH$_2$), 4.02 (s, 2H, CH$_2$), 6.59 (s, 1H, fumarate), 7.18–7.62 (m, 8H, Ar—H). $^{13}$C NMR (DMSO-d$_6$) δ: 35.77, 38.50, 42.20, 49.94, 55.85, 67.28, 125.43, 126.39, 126.56, 127.89, 134.56, 136.19, 143.03, 166.67. Anal. Calcd. For (C$_{18}$H$_{19}$N.C$_4$H$_4$O$_4$.0.25H$_2$O): C, 71.42; H, 6.40; N, 3.78. Found. C, 71.68; H, 6.68; N, 3.75

Example 3

Synthesis of Spiro[9,10-dihydroanthracene]-9,3'-(1-benzyl)-pyrrolidine [7]

The synthesis of compound [7] was from [5] was carried out as depicted in Scheme 3 and as described below. Regarding Scheme 3, reagents and conditions were as follows: C$_6$H$_5$CH$_2$Br, Et$_3$N, CH$_2$Cl$_2$, reflux.

Scheme 3

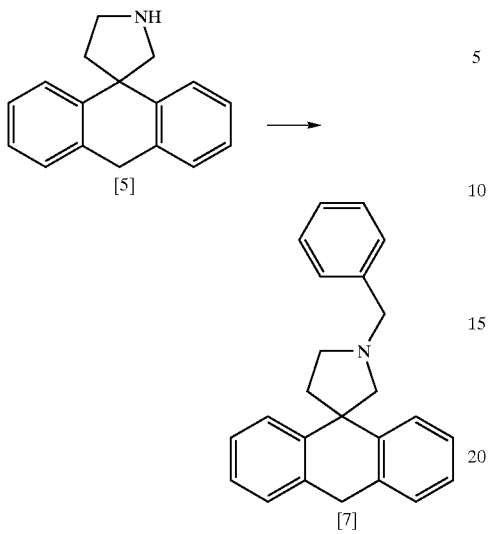

Spiro[9,10-dihydroanthracene]-9,3'-pyrrolidine [5] (0.125 g, 0.53 mmol) was dissolved in anhydrous $CH_2Cl_2$ (10 mL) and triethylamine was added dropwise. The reaction mixture was cooled in an ice-bath and benzyl bromide (0.113 g, 0.66 mmol) in anhydrous $CH_2Cl_2$ (5 mL) was added via syringe. The reaction mixture was warmed to room temperature and then heated at reflux (4 h). The solvent was removed under reduced pressure and water (20 mL) was added to the residue and extracted with EtOAc (3×25 mL). The combined EtOAc extracts were washed with water, brine, dried ($MgSO_4$) and evaporated under reduced pressure to give a dark brown oil which was purified by mplc using $CH_2Cl_2$ as eluent to give 0.12 g (70%) of the amine as a colorless oil. The oil was dissolved in anhydrous acetone and fumaric acid (0.047 g, 0.40 mmol) was added and heated to dissolve the acid. The solution on cooling gave the product as a white powder: mp. 175–176° C. (EtOAc—$CH_3OH$). $^1H$ NMR (DMSO-$d_6$)δ: 2.31–2.35 (t, J=6 Hz, 2H, $CH_2$), 2.87–2.92 (t, J=7.5 Hz, 2H, $CH_2$), 3.02 (s, 2H, $CH_2$), 3.74 (s, 2H, $CH_2$), 3.98 (s, 2H, $CH_2$), 6.61 (s, 1H, fumarate), 7.14–7.66 (m, 8H, Ar—H). $^{13}C$ NMR (DMSO-$d_6$) δ: 35.56, 49.22, 53.81, 59.68, 66.15, 125.67, 126.19, 126.53, 127.28, 127.78, 128.60, 128.81, 134.40, 135.83, 143.92, 166.39. Anal. Calcd. For ($C_{24}H_{23}N.C_4H_4O_4$): C, 76.16; H, 6.16; N, 3.17. Found. C, 76.08; H, 6.25; N, 3.21

Example 4

Synthesis of Spiro[-(10,10-dimethyl)-9,10-dihydroanthracene]-9,3'-pyrrolidine [12]

Compound 12 was synthesized as depicted in Scheme 4 and as described below. Referring to Scheme 4, reagents and conditions were as follows: (a) $POCl_3$, reflux, 45 min, (b) $C_2H_5ONa$, $BrCH_2COOC_2H_5$, EtOH, reflux, (c) 10% Pd/C, $CH_3OH$, HCl, (d) Borane-THF/THF; 6.0M HCl.

Scheme 4

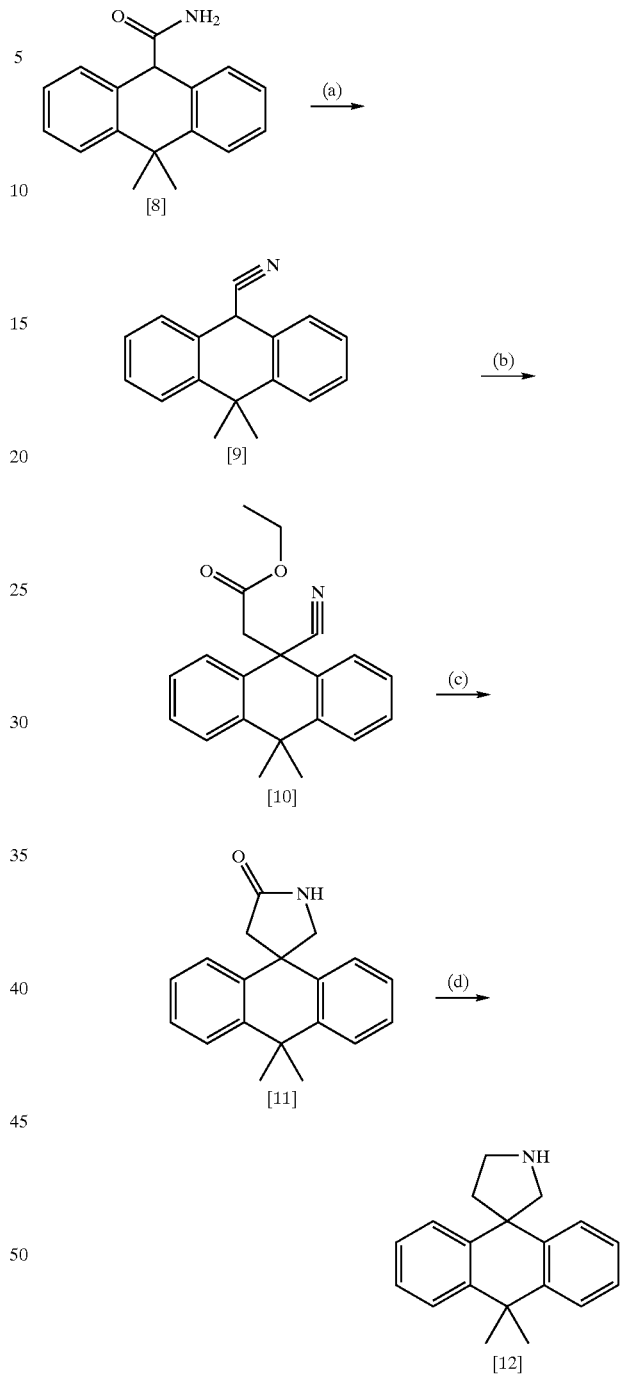

9-cyano-10,10-Dimethyl-9,10-dihydroanthracene [9]

$POCl_3$ (25 mL, 00 mmol) was added to crystalline 10,10-Dimethyl-9,10-dihydroanthracene-9-carboxamide [8] (1.25 g, 4.9 mmol) while stirring. The solution was then heated at reflux (30 min), when TLC showed complete absence of starting material. The solution was then poured into a mixture of crushed ice and $NH_4OH$ with vigorous stirring. The solution was stirred for 15 minutes and excess of $NH_4OH$ was added to keep the solution alkaline. A solid substance separated out which was extracted with ether (3×50 ml). The combined ether extracts were washed with water, brine, dried ($MgSO_4$) and evaporated under reduced pressure to give an light yellow oil which crystallized immediately. The product obtained was chromatographically pure and recrystallized readily from EtOH to give 1.0 g (86%) of the product as colorless prisms. mp. 91–92° C. $^1$H NMR (CDCl$_3$)d: 1.54 (s, 3H, CH$_3$), 1.79 (s, 3H, CH$_3$), 5.32 (s, 1H, CH), 7.32–7.68 (m, 8H, Ar—H). $^{13}$C NMR (CDCl$_3$)d: 30.22, 30.33, 36.95, 125.77, 127.43, 127.92, 129.28. Anal. Calcd. For (C$_{17}$H$_{15}$N): C, H, N.

(9-Cyano-10,10-dimethyl-9,10-dihydro-anthracen-9-yl)-acetic acid ethyl ester [10]

9-cyano-10,10-Dimethyl-9,10-dihydroanthracene [9] (0.8 g, 3.42 mmol) was added to sodium ethoxide prepared from Na metal (0.110 g, 4.80 mmol) and ethanol (10 mL) and heated under reflux for one hour leading to the development of a greenish brown solution. The solution was then cooled in an ice bath and ethyl bromoacetate (0.80 g, 4.80 mmol) was added dropwise via a syringe. The resulting mixture was then heated at reflux (4 h) and filtered. The solid residue was washed with ether (25 mL). Water (25 mL) was added to the filtrate and the organic layer was separated. The aqueous layer was once again extracted with ether (25 mL). The combined ether extracts were washed with water, brine, dried (MgSO$_4$) and evaporated under reduced pressure to give an oil which was purified by medium pressure liquid chromatography using pet. ether: EtOAc (9:1) as eluent to give 0.978 g (74%) of the product as a colorless oil. $^1$H NMR (CDCl$_3$)d: 0.98–1.06 (t, 3H, CH$_3$), 1.64–1.67 (d, J=9Hz, 3H, CH$_3$), 1.71–1.74 (d, J=9 Hz, 3H, CH$_3$), 3.04–3.07 (d, J=9Hz, 2H, CH$_2$), 3.86–3.94 (q, 2H, CH$_2$), 7.29–7.77 (m, 8H, Ar—H). $^{13}$C NMR (CDCl$_3$)d: 14.39, 33.85, 35.21, 38.37, 52.29, 61.38, 123.17, 127.53, 127.84, 128.17, 129.48, 130.97, 143.23, 167.97.

Spiro[-(10,10-dimethyl)-9,10-dihydroanthracene]-9,4'-pyrrolidin-2'-one [11]

A mixture of(9-Cyano- 10,10-dimethyl-9,10-dihydro-anthracen-9-yl)-acetic acid ethyl ester [10] (0.975 g, 3.05 mol), 10% Pd/C (0.1 g) in methanol (20 mL) and HCl (1 mL) was hydrogenated at 50 kg/cm$^3$ (24 h). The catalyst was filtered off with celite and the solvent was evaporated under reduced pressure to give a white semisolid. Water (25 mL) was added and the solution was made basic with 10% NaOH and extracted with EtOAc (3×25 mL). The combined EtOAc extracts were washed with water, brine and dried using anhydrous MgSO$_4$ and evaporated under reduced pressure to give a colorless oil which was purified by mplc using pet.ether: EtOAc (8:2) as eluent to give a white solid. The solid was recrystallized from CHCl$_3$-pet.ether to give 0.4 g (40%) of the pure amide as colorless needles. mp 236–237° C. $^1$H NMR (CDCl$_3$)d: 1.68 (s, 6H, CH3), 3.07 (s, 2H, CH$_2$), 3.97 (s, 2H, CH$_2$), 7.32–7.56 (m, 8H, Ar—H). $^{13}$C NMR (CDCl$_3$)d: 35.17, 35.26, 37.89, 43.67, 53.34, 63.86, 126.68, 126.98, 127.70, 128.00, 141.14, 142.47, 178.04

Spiro[-(10,10-dimethyl)-9,10-dihydroanthracene]-9,3'-pyrrolidine [12]

A 1.0M solution of BH$_3$-THF complex (7.00 ml, 7.00 mmol) was added at 0° C. to a well stirred solution of Spiro[-(10,10-dimethyl)-9,10-dihydroanthracene]-9,4'-pyrrolidin-2'-one [11] (0.15 g, 0.54 mmol) in anhydrous THF (2 mL). The solution was brought to room temperature and then heated at reflux (8 h), cooled and 6 M solution of HCl (4 mL) was added cautiously to the reaction mixture. The reaction mixture was then heated at reflux for an additional hour, cooled and the solvent was removed under reduced pressure, resulting in a white suspension. Water (20 mL) was added to it and extracted with EtOAc (20 mL). The aqueous phase was then basified using 10% NaOH and the resultant solution was extracted with Et$_2$O (3×25 ml). The combined Et$_2$O extracts were washed with water, brine, dried (MgSO$_4$) and the solvent was removed under reduced pressure to give 0.129 g (90%) the amine as a colorless oil. The oil was dissolved in anhydrous acetone and fumaric acid (0.062 g, 0.538 mmol) was added and heated. The solution on cooling gave the fumarate as a white powder: mp. 207–208° C. (EtOAc—CH$_3$OH). $^1$H NMR (DMSO-d$_6$)d: 1.57 (s, 3H, CH$_3$), 1.63 (s, 3H, CH$_3$), 2.31–2.36 (t, J=7.5 Hz, 2H, CH$_2$), 3.51–3.56 (t, J=7.5 Hz, 2H, CH$_2$), 3.63 (s, 2H, CH$_2$), 6.53 (s, 1H, fumarate), 7.27–7.64 (m, 8H, Ar—H). $^{13}$C NMR (DMSO-d$_6$) δ: 33.77, 35.19, 37.67, 47.00, 48.70, 48.88, 63.75, 126.70, 127.17, 135.39, 140.55, 142.59, 168.28. Anal. Calcd. For (C$_{19}$H$_{21}$N.C$_4$H$_4$O$_4$): C, 72.80; H, 6.64; N, 3.69. Found C, 72.40, 6.64, 3.65

Example 5

Synthesis of Spiro[-(3-methoxy)-9,10-dihydroanthracene]-9,3'-pyrrolidine [17]

The compound [17] was synthesized as depicted in Scheme 5 and described below. Referring to Scheme 5, reagents and conditions were as follows: (a) 2-Bromobenzaldehyde, anhydrous THF, 0° C. (b) LiAlH$_4$/AlCl$_3$, anhydrous Et$_2$O, reflux (c) n-BuLi, anhydrous Et$_2$O, n-benzyl-3-pyrrolidone (d) CH$_3$SO$_3$H, rt (e) 10% Pd/C, CH$_3$OH.

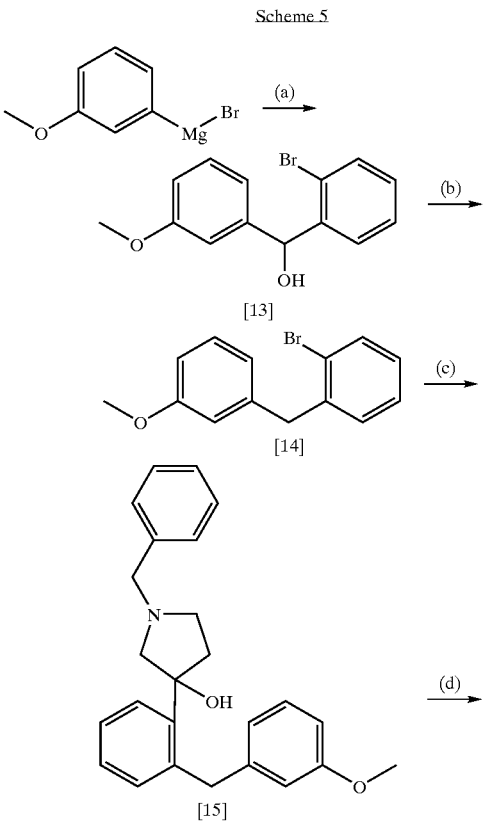

Scheme 5

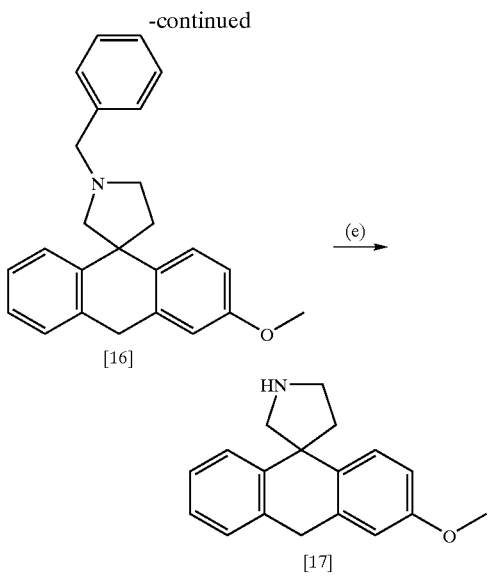

(2-Bromo-phenyl)-(3-methoxy-phenyl)-methanol [13]

3-Methoxyphenyl magnesium bromide (1.0 M solution in THF; 5.4 mL, 5.4 mmol) was taken in a flask under $N_2$ and cooled (0° C.). 2-Bromobenzaldehyde (1 g, 5.4 mmol) in anhydrous THF (10 mL) was added dropwise via syringe over 5 min. The reaction mixture was stirred at this temperature for 20 min. and slowly brought to room temperature. After stirring for another 30 min. satd. $NH_4Cl$ solution (20 mL) was added and the mixture was extracted with $Et_2O$ (3×25 mL). The combined $Et_2O$ extracts were washed with water, brine, dried ($MgSO_4$) and evaporated under reduced pressure to give a yellow oil. The oil was purified by mplc using $CH_2Cl_2$ as eluent to give 1.275 g (81%) of the alcohol as a colorless oil. $^1H$ NMR ($CDCl_3$)d: 2.71 (s, 1H, OH), 3.78 (s, 3H, $CH_3$), 6.15 (s, 1H, CH), 6.80–7.58 (m, 8H, Ar—H). $^{13}C$ NMR ($CDCl_3$)d: 55.80, 75.16, 113.29, 119.90, 123.39, 128.33, 129.11, 129.71, 130.08, 133.39.

3-(2-Bromobenzyl)-methoxy benzene [14]

$LiAlH_4$ (0.154 g, 4.06 mmol) was suspended in anhydrous $Et_2O$ (10 mL) under a $N_2$ atmosphere and cooled (0° C.) with stirring. Anhydrous $AlCl_3$ (1.08 g, 8.14 mmol)was dissolved in ice-cold anhydrous $Et_2O$ (20 mL) and added dropwise to the $LiAlH_4$ suspension. After complete addition the suspension was stirred at the same temperature (20 min.). (2-Bromo-phenyl)-(3-methoxy-phenyl)-methanol [13] (0.68 g, 2.32 mmol) was dissolved in anhydrous $Et_2O$ (10 mL) and added dropwise via syringe to the suspension. After complete addition the reaction mixture was heated at reflux (4 h), cooled (0° C.) and EtOAc was added dropwise to destroy the excess of the reagent and the mixture was added to 20% aq. $H_2SO_4$ (50 mL). $Et_2O$ (50 mL) was added and extracted. The $Et_2O$ layer was separated, washed with water, brine, dried ($MgSO_4$) and evaporated to give a reddish yellow oil. The oil was purified by mplc using pet. ether-$CH_2Cl_2$ (9:1) as eluent to give 0.485 g (75%) of the pure product as a colorless oil. $^1H$ NMR ($CDCl_3$)d: 3.81 (s, 3H, $CH_3$), 4.14 (s, 2H, $CH_2$), 6.79–7.62 (m, 8H, Ar—H). $^{13}C$ NMR ($CDCl_3$)d: 42.34, 55.69, 112.07, 122.02, 125.48, 128.07, 128.50, 130.02, 131.66, 133.43.

1-Benzyl-3-[2-(3-methoxy-benzyl)-phenyl]-pyrrolidin-3-ol [15]

3-(2-Bromobenzyl)-methoxy benzene (0.5 g, 1.80 mmol) [14] was dissolved in anhydrous $Et_2O$ (15 mL)and cooled to −78° C. under $N_2$. n-butyl lithium (0.8 mL, 1.98 mmol, 2.5M soln. in $Et_2O$) was added dropwise over 5 min. and stirred for 30 min. The reaction mixture was then brought to room temperature over 1 hr. The reaction mixture was cooled to −78° C. and n-benzyl-3-pyrrolidone (0.31 mL, 1.9 mmol) in anhydrous $Et_2O$ (5 mL) was added via syringe with stirring. The reaction mixture was brought to room temperature over 3 hr. Water (50 mL) was added and the organic phase was extracted. The aqueous phase was extracted with $Et_2O$ (50 mL) and the combined $Et_2O$ extracts were washed with water, brine and dried ($MgSO_4$). $Et_2O$ was removed under reduced pressure to give a red oil which was purified by mplc using $CH_2Cl_2$:$(CH_3)_2CO$ (9:1) as eluent to give 0.3 g (45%) of the aminoalcohol as a dark yellow oil. A small sample was converted into its filmarate, mp 148–149° C. (EtOAc—$CH_3OH$). $^1H$ NMR (DMSO-$d_6$)d: 2.11–2.40 (m, 2H, $CH_2$), 2.96–2.99 (d, 4H, $CH_2$), 3.23–3.27 (d, 1H, OH), 3.67 (s, 3H, $CH_3$), 3.89 (s, 2H, $CH_2$), 4.27 (s, 2H, $CH_2$), 6.58–7.42 (m, 14H, Ar—H). $^{13}C$ NMR ($CDCl_3$)d: 38.21, 52.70, 55.21, 59.71, 66.46, 80.27, 111.23, 115.17, 121.54, 125.84, 125.97, 127.38, 127.86, 128.67, 129.38, 129.58, 132.17, 134.71, 139.49, 143.93, 159.37, 160.97.

3-Methoxy-9,9-[spiro-3'-(n-benzyl)-pyrrolidinyl]-9,10-dihydroanthracene [16]

Methanesulfonic acid (5 mL) was added to 1-Benzyl-3-[2-(3-methoxy-benzyl)-phenyl]-pyrrolidin-3-ol [15] (0.5 g, 1.33 mmol) taken in a round bottom flask equipped with a stirrer under $N_2$ at room temperature. Stirring was continued (30 min.), when TLC showed absence of starting material. Crushed ice/water was added to the reaction mixture and the solution was made basic by the addition of 10% NaOH. The alkaline reaction mixture was extracted with EtOAc (3×25 mL). The combined EtOAc extracts were washed with water, brine and dried ($MgSO_4$). EtOAc was removed under reduced pressure to give a red oil which was purified by mplc using $CH_2Cl_2$:$(CH_3)_2CO$ (9:1) as eluent to give 0.24 g (52%) of the amine as a colorless oil. The oil was converted into its oxalate salt mp. 187–188° C. (Acetone). Anal. Calcd. For ($C_{25}H_{25}NO.C_2H_2O_4$): C, 72.79; H, 6.10; N, 3.14. Found. C, 72.75; H, 6.15; N, 3.11. $^1H$ NMR (DMSO-$d_6$)d: 2.52 (s, 2H, $CH_2$), 3.27 (bs, 2H, $CH_2$), 3.40 (s, 2H, $CH_2$), 3.77 (s, 3H, $CH_3$), 4.00 (s, 2H, $CH_2$), 4.13 (s, 2H, $CH_2$) 6.82–7.63 (m, 12H, Ar—H). $^{13}C$ NMR (DMSO-$d_6$)d: 35.60, 48.56, 52.92, 54.98, 58.54, 111.67, 112.74, 124.45, 125.75, 126.18, 127.59, 128.08, 128.42, 129.57, 135.96, 137.52, 155.71, 157.52, 162.69.

3-Methoxy-9,9-[spiro-3'-pyrrolidinyl]-9,10-dihydroanthracene [17]

3-Methoxy-9,9-[spiro-3'-(n-benzyl)-pyrrolidinyl]-9,10-dihydroanthracene [16] (0.23 g, 0.647 mmol) was dissolved in $CH_3OH$ (15 mL) and 10% Pd/C (0.050 g) was added under $N_2$. A few drops of HCl were added and the reaction mixture was hydrogenated on a parr-hydrogenator at 50 psi overnight and the catalyst was filtered off using celite. The filterate was evaporated and water (15 mL) was added and basified using 10% NaOH. The basic solution was extracted with $CH_2Cl_2$ (2×25 mL) and the combined extracts were washed with water, brine and dried ($MgSO_4$). The $CH_2Cl_2$ was removed under reduced pressure to give a yellow oil which was purified by mplc using $CH_2Cl_2$:$CH_3OH$ (9:1) as eluent to give 0.126 g (74%) of the product as a colorless oil which darkened rapidly. The oil was converted into its oxalate salt, mp. 99–101° C. (Acetone). Anal. Calcd. For ($C_{18}H_{19}NO.C_2H_2O_4.0.5(CH_3)_2CO.0.5H_2O$): C, 65.63; H, 6.40; N, 3.56. Found. C, 65.39; H, 5.99; N, 3.31. $^1H$ NMR ($CDCl_3$)d: 2.32–2.38 (m, 2H, $CH_2$), 2.97–3.02 (t, J=15 Hz, 2H, $CH_2$), 3.18 (bs 2H, $CH_2$), 3.83 (s, 3H, $CH_3$), 4.05 (bs, 2H, $CH_2$), 6.79–7.77 (m, 7H, Ar—H). $^{13}C$ NMR ($CDCl_3$)d:

36.75, 41.94, 52.78, 55.27, 65.73, 112.93, 125.87, 126.24, 126.90, 127.47, 128.01, 128.80, 129.61.

Example 6

Synthesis of 3-Hydroxy-9,9-[spiro-3'-(n-benzyl)-pyrrolidinyl]-9,10-dihydroanthracene [18]

Compound 18 was synthesized as depicted in Scheme 6 and described below. Referring to Scheme 6, reagents and conditions were as follows: BBr$_3$, CH$_2$Cl$_2$, −78° C.

Scheme 6

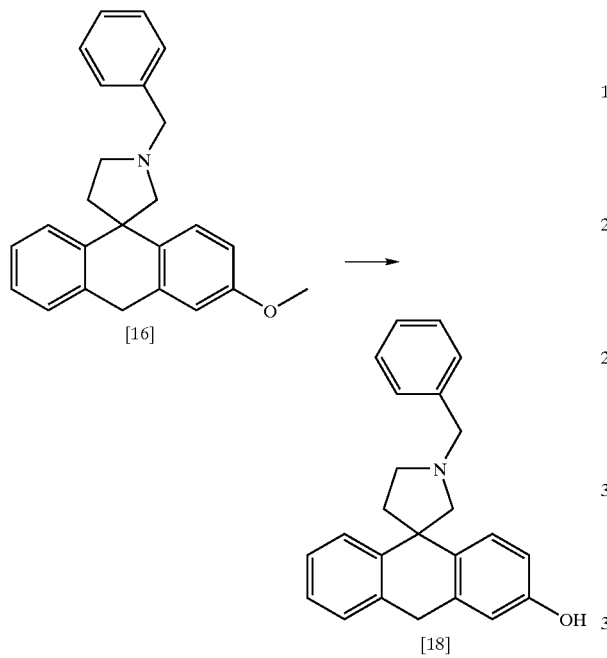

To a solution of 3-Methoxy-9,9-[spiro-3'-(n-benzyl)-pyrrolidinyl]-9,10-dihydroanthracene [16] (0.24 g, 0.675 mmol) in anhydrous CH$_2$Cl$_2$ (10 mL) at −78° C. was added BBr$_3$ (2.70 mL, 2.7 mmol, 1M soln. in CH$_2$Cl$_2$) dropwise. The temperature was raised to ambient temperature over a period of 2 hr. and stirring was continued for 6 hr. The reaction mixture was cooled to −78° C. and CH$_3$OH (5 mL) was added dropwise via syringe and the solvent was removed under reduced pressure. The residue was redissolved in CH$_3$OH and satd. Solution of NaHCO$_3$ was added and extracted with Et$_2$O (2×25 mL). The combined Et$_2$O extracts were washed with water, brine and dried (MgSO$_4$). The solvent was removed under reduced pressure to give a dark yellow oil. The oil was purified by mplc using CH$_2$Cl$_2$: (CH$_3$)$_2$CO (9:1) as eluent to give 0.21 g (91%) the product as a pale yellow oil. The oil was converted into its oxalate salt mp. 133–134° C. (EtOAC—CH$_3$OH). Anal. Calcd. For (C$_{24}$H$_{23}$NO.C$_2$H$_2$O$_4$.0.5H$_2$O): C, 70.89; H, 5.94; N, 3.17. Found. C, 70.90; H, 5.88; N, 3.30. $^1$H NMR (DMSO-d$_6$)d: 2.50 (bs, 2H, CH$_2$), 3.30 (bs, 2H, CH$_2$), 3.42 (bs, 2H, CH$_2$), 3.91 (bs, 2H, CH$_2$), 4.17 (bs, 2H, CH$_2$), 6.65–7.57 (m, Ar—H, 12H). $^{13}$C NMR (DMSO-d$_6$)d: 36.41, 49.40, 53.69, 59.25, 64.40, 113.81, 115.09, 127.08, 129.34, 130.77, 132.40, 137.05, 138.24, 142.73, 156.49, 164.15, 208.92.

Example 7

Synthesis of Spiro[-(3-hydroxy)-9,10-dihydroanthracene]-9,3'-pyrrolidine [19]

Compound [19] was synthesized as depicted in Scheme 7 and described below. Referring to Scheme 7, reagents and conditions were as follows: BBr$_3$, CH$_2$Cl$_2$, −78° C.

Scheme 7

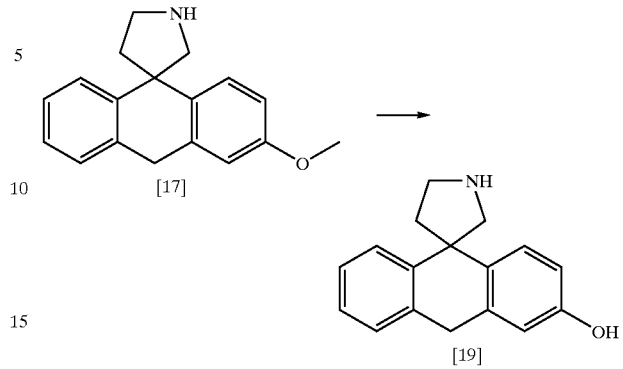

Spiro[-(3-methoxy)-9,10-dihydroanthracene]-9,3'-pyrrolidine [17] (0.2 g, 0.756 mmol) was dissolved in anhydrous CH$_2$Cl$_2$ (10 mL) and cooled to −78° C. under N$_2$. BBr$_3$ (3.78 mL, 1.0M soln. in CH$_2$Cl$_2$) was added dropwise via syringe over 15 min. The reaction mixture was allowed to stir at room temperature overnight and cooled to −78° C. Anhydrous CH$_3$OH (5 mL) was added dropwise and the solvents were evaporated under reduced pressure to give a dry solid. The solid was redissolved in anhydrous CH$_3$OH (5 mL) and EtOAc (35 mL) was added and cooled. The product crystallized as a pale white solid, which was once again recrystallized from EtOAc—CH$_3$OH to give 0.15 g (60%) of the product as its hydrobromide, mp. 150–151° C. (dec.). $^1$H NMR (DMSO-d$_6$)d: 2.32–2.36 (t, J=6 Hz, 2H, CH$_2$), 3.39 (bs, 2H, CH$_2$), 3.71 (bs, 2H, CH$_2$), 3.99 (bs, 2H, CH$_2$), 6.65–7.54 (m, 7H, Ar—H), 9.28 (bs, 1H). $^{13}$C NMR (DMSO-d$_6$)d: 35.86, 44.43, 49.37, 51.93, 112.80, 114.76, 124.76, 126.24, 126.74, 127.98, 129.50, 137.06, 138.30, 139.80, 156.04, 195.17. Anal. Calcd. For (C$_{17}$H$_{17}$NO.HBr.0.5H$_2$O): C, 59.83; H, 5.61; N, 4.10. Found. C, 59.35; H, 5.48; N, 3.60.

Example 8

Synthesis of 3-n-Hexyl-9,9-[spiro-3'-pyrrolidinyl]-9,10-dihydroanthracene [21]

Compound [21] was synthesized as depicted in Scheme 8 and as described below. Referring to Scheme 8, reagents and conditions were as follows: (a) Triflic anhydride, C$_5$H$_5$N (b) 1-hexene, 9-BBN, PdCl$_2$(dppf), K$_3$PO$_4$, anhyd. THF (c) 10% Pd/C, CH$_3$OH, HCl.

Scheme 8

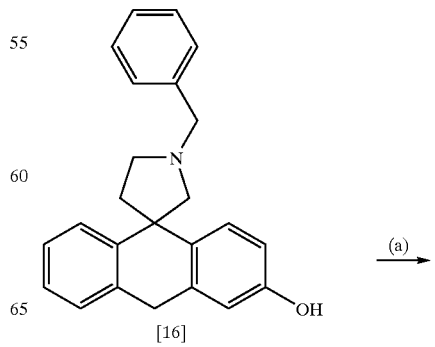

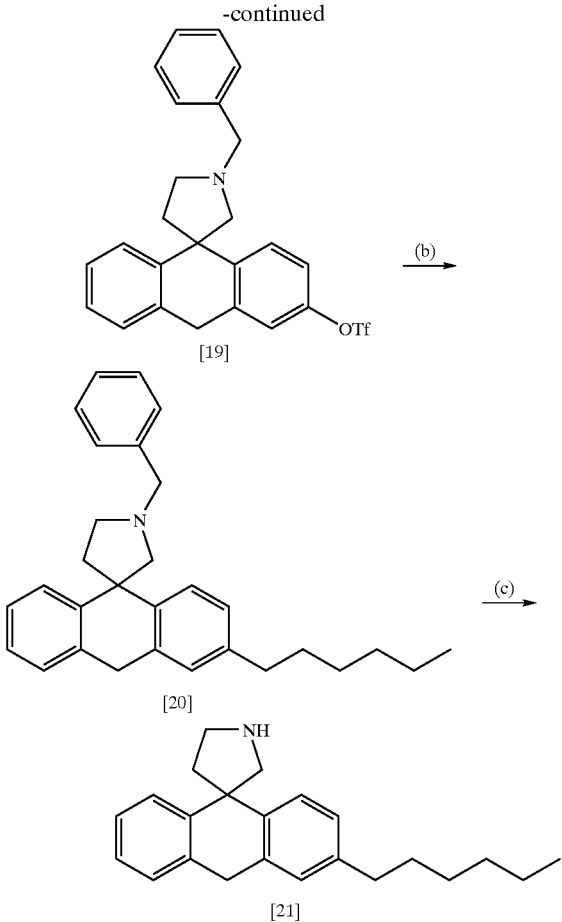

3-Trifluoromethane sulfonyl oxy-9,9-[spiro-3'-(n-benzyl)-pyrrolidinyl]-9,10-dihydroanthracene [19]

To a solution of 3-Hydroxy-9,9-[spiro-3'-(-benzyl)-pyrrolidinyl]-9,10-dihydro-anthracene [16] (0.765 g, 2.241 mmol) in pyridine (5 mL) at 0° C. was added triflic anhydride (0.961 g. 0.58 mL, 3.4 mmol) dropwise via syringe under $N_2$. The reaction mixture was gradually brought to room temperature and stirred (3 hr.). Crushed ice/water was added and the solution was extracted with $Et_2O$ (2×25 mL). The combined $Et_2O$ extracts were washed with water, brine, dried ($MgSO_4$) and evaporated under reduced pressure to give a red oil. The oil was purified by mplc using pet. Ether:acetone (9:1) as eluent giving 0.93 g (85%) of the triflate as a reddish brown oil. $^1H$ NMR ($CDCl_3$)d: 2.34–2.40 (m, 2H, $CH_2$), 2.85–2.88 (m, 2H, $CH_2$), 2.99–3.15 (m, 2H, $CH_2$), 3.76 (s, 2H, $CH_2$), 4.02–4.05 (m, 2H, $CH_2$), 7.13–7.84 (m, 12H, Ar—H). $^{13}C$ NMR ($CDCl_3$)d: 35.43, 48.73, 53.95, 59.92, 66.59, 118.58, 121.77, 126.54, 128.31, 133.85, 137.46, 142.69, 144.88, 147.18

3-n-Hexyl-9,9-[spiro-3'-(n-benzyl)-pyrrolidinyl]-9,10-dihydroanthracene [20]

An oven dried flask equipped with a septum inlet and condenser was flushed with $N_2$ and charged with a soln. of 9-BBN (2.15 mL, 1.079 mmol, 0.5 M soln.), cooled to 0° C. and 1-hexene (0.133 mL, 1.079 mmol) was added via syringe. The mixture was brought to room temperature and stirred (8 hr.). To the prepared BBN soln. was added $K_3PO_4$ (0.312 g, 1.471 mmol), $PdCl_2$(dppf) (0.020 g, 5 mol %) and 3-Trifluoromethane sulfonyl oxy-9,9-[spiro-3'-(n-benzyl)-pyrrolidinyl]-9,10-dihydroanthracene [19] (0.48 g, 0.980 mmol) in anhydrous THF (10 mL). The reaction mixture was heated at reflux overnight, cooled and water (20 mL) was added. The reaction mixture was then extracted with EtOAc (3×25 mL). The combined EtOAc extracts were washed with water, brine and dried ($MgSO_4$). The solvent was removed under reduced pressure to give a dark brown oil, which was purified by mplc using pet. Ether-EtOAc (9:1) as eluent to give 0.34 g (85%) of the product as an yellow oil. The oil was converted into its oxalate, mp. 135–136° C. (EtOAc—$CH_3OH$). $^1H$ NMR ($CDCl_3$)d: 0.87 2.34–2.40 (bm, 13H, $CH_2$), 2.30–2.42 (bm, 2H, $CH_2$), 2.62 (bs, 2H, $CH_2$), 2.93 (bs, 2H, $CH_2$), 3.13 (bs, 2H, $CH_2$), 3.75 (bs, 2H, $CH_2$), 4.00 (bs, 2H, $CH_2$), 7.04–7.72 (m, 12H, Ar—H). $^{13}C$ NMR ($CDCl_3$)d: 27.19, 28.87, 35.62, 35.77, 41.37, 48.69, 54.26, 60.14, 67.07, 111.26, 123.54, 125.55, 126.06, 126.58, 127.24, 128.02, 128.37, 134.70, 134.77, 135.04, 139.33, 139.55, 140.14, 140.32, 142.28, 144.18. Anal. Calcd. For ($C_{30}H_{35}N \cdot C_2H_2O_4 \cdot 0.5H_2O$): C, 75.56; H, 6.52; N, 2.75. Found. C, 75.04; H, 6.76; N, 2.91.

3-n-Hexyl-9,9-[spiro-3'-pyrrolidinyl]-9,10-dihydro-anthracene [21]

3-n-Hexyl-9,9-[spiro-3'-(n-benzyl)-pyrrolidinyl]-9,10-dihydroanthracene [20] (0.20 g, 0.488 mmol) was dissolved in $CH_3OH$ (15 mL) and 10% Pd/C (0.050 g) was added under $N_2$. A few drops of HCl were added and the reaction mixture was hydrogenated on a parr-hydrogenator at 50 psi overnight and the catalyst was filtered off using celite. The filtrate was evaporated and water (15 mL) was added and basified using 10% NaOH. The basic solution was extracted with $CH_2Cl_2$ (2×25 mL) and the combined extracts were washed with water, brine and dried ($MgSO_4$). The $CH_2Cl_2$ was removed under reduced pressure to give a yellow oil which was purified by mplc using $CH_2Cl_2:CH_3OH$ (9:1) as eluent to give 0.11 g (70%) of the product as a colorless oil which darkened rapidly. The oil was converted into its oxalate salt, mp. 110–111° C. (EtOAc—$CH_3OH$). $^1H$ NMR ($CDCl_3$)d: 0.83–0.89 (m, 2H, $CH_2$), 1.21–1.31 (m, 9H, $CH_2$), 2.36–2.40 (t, J=6 Hz, 2H, $CH_2$), 2.56–2.61 (t, J=6 Hz, 2H, $CH_2$), 3.49 (bs, 2H, $CH_2$), 3.74 (bs, 2H, $CH_2$), 4.03 (bs, 2H, $CH_2$), 7.11–7.54 (m, 7H, Ar—H). Anal. Calcd. For ($C_{23}H_{29}N \cdot C_2H_2O_4 \cdot 0.25H_2O$): C, 72.52; H, 7.66; N, 3.38. Found. C, 72.29; H, 7.55; N, 3.15.

Example 9

Synthesis of 3-(3-Phenylpropyl)-9,9-[spiro-3'-pyrrolidinyl]-9,10-dihydroanthracene [23]

Compound [23] was synthesized as depicted in Scheme 9 and as described below. Referring to Scheme 9, reagents and conditions were as follows: (a) allyl benzene, 9-BBN, $PdCl_2$(dppf), $K_3PO_4$, anhyd. THF (b) 10% Pd/C, $CH_3OH$, HCl Scheme 9

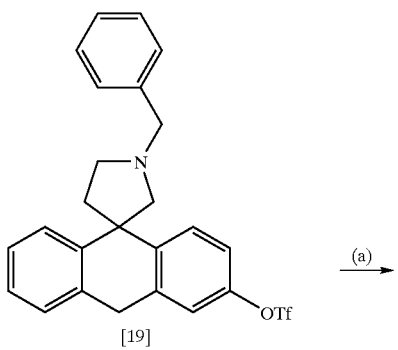

-continued

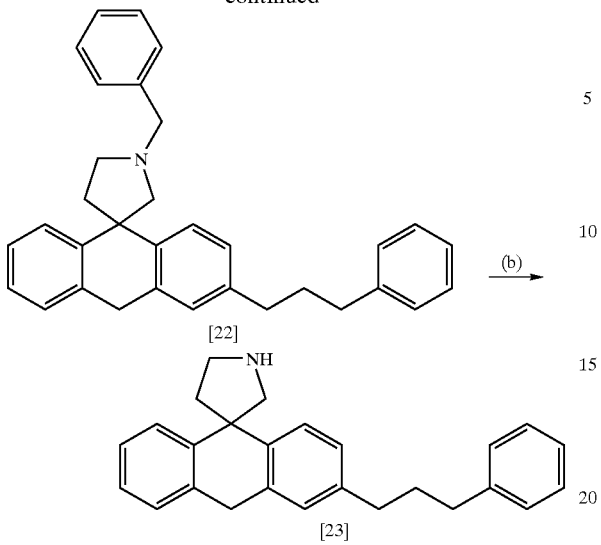

[22]

[23]

3-(3-Phenylpropyl)-9,9-[spiro-3'-(n-benzyl)-pyrrolidinyl]-9,10-dihydroanthracene [22]

An oven dried flask equipped with a septum inlet and condenser was flushed with $N_2$ and charged with a soln. of 9-BBN (2.15 mL, 1.079 mmol, 0.5 M soln.), cooled to 0° C. and allyl benzene (0.142 mL, 1.079 mmol) was added via syringe. The mixture was brought to room temperature and stirred (8 hr.). To the prepared BBN soln. was added $K_3PO_4$ (0.312 g, 1.471 mmol), $PdCl_2$(dppf) (0.020 g, 5 mol %) and 3-Trifluoromethane sulfonyl oxy-9,9-[spiro-3'-(n-benzyl)-pyrrolidinyl]-9,10-dihydroanthracene [19] (0.48 g, 0.980 mmol) in anhydrous THF (10 mL). The reaction mixture was heated at reflux overnight, cooled and water (20 mL) was added. The reaction mixture was then extracted with EtOAc (3×25 mL). The combined EtOAc extracts were washed with water, brine and dried ($MgSO_4$). The solvent was removed under reduced pressure to give a dark brown oil, which was purified by mplc using pet. Ether-EtOAc (9:1) as eluent to give 0.22 g (52%) of the product as an yellow oil. The oil was converted into its oxalate, mp. 137–138° C. (EtOAc—$CH_3OH$). $^1H$ NMR (DMSO-$d_6$)d: 1.55 (bs, 4H, $CH_2$), 2.47 (s, 4H, $CH_2$), 3.21 (s, 2H, $CH_2$), 3.38 (s, 2H, $CH_2$), 3.94–3.98 (d, J=12Hz, 2H, $CH_2$), 4.07 (s, 2H, $CH_2$). $^{13}C$ NMR ($CDCl_3$)d: 21.61, 25.82, 31.63, 35.57, 48.63, 59.90, 61.83, 70.58, 125.40, 125.96, 126.45, 127.82, 128.20, 134.73, 135.12, 137.9, 139.04, 142.86, 143.77. Anal. Calcd. For($C_{33}H_{33}N.C_2H_2O_4.H_2O$): C, 76.20; H, 6.76; N, 2.53. Found. C, 76.11; H, 6.54; N, 2.94.

3-(3-Phenylpropyl)-9,9-[spiro-3'-pyrrolidinyl]-9,10-dihydroanthracene [23]

3-(3-Phenylpropyl)-9,9-[spiro-3'-(n-benzyl)-pyrrolidinyl]-9,10-dihydroanthracene [22] (0.20 g, 0.451 mmol) was dissolved in $CH_3OH$ (15 mL) and 10% Pd/C (0.050 g) was added under $N_2$. A few drops of HCl were added and the reaction mixture was hydrogenated on a parr-hydrogenator at 50 psi overnight and the catalyst was filtered off using celite. The filterate was evaporated and water (15 mL) was added and basified using 10% NaOH. The basic solution was extracted with $CH_2Cl_2$ (2×25 mL) and the combined extracts were washed with water, brine and dried ($MgSO_4$). The $CH_2Cl_2$ was removed under reduced pressure to give a yellow oil which was purified by mplc using $CH_2Cl_2$:$CH_3OH$ (9:1) as eluent to give 0.071 g (45%) of the product as a colorless oil which darkened rapidly. The oil was converted into its oxalate salt, mp. 81–82° C. (EtOAc—$CH_3OH$). $^1H$ NMR (DMSo-$d_6$)d: 1.57–1.71 (bd, 4H, $CH_2$), 2.38 (s, 2H, $CH_2$), 2.47 (s, 2H, $CH_2$), 3.38 (s, 2H, $CH_2$), 3.77 (s, 2H, $CH_2$), 4.07 (s, 2H, $CH_2$), 7.27–7.52 (bm, 7H, Ar—H). Anal. Calcd. For ($C_{26}H_{27}N.C_2H_2O_4.2H_2O$): C, 70.12; H, 6.93; N, 2.92. Found. C, 69.45; H, 6.34; N, 3.66.

Example 10

Synthesis of 3-(3-Phenyl)-9,9-[spiro-3'-pyrrolidinyl]-9,10-dihydroanthracene [25]

Compound [25] was synthesized as depicted in Scheme 10 and as described below. Referring to Scheme 10, reagents and conditions were as follows: (a) Phenyl boronic acid, $[(C_6H_5)_3P]_4Pd$, $K_2CO_3$, anhyd. toluene (b) 10% Pd/C, $CH_3OH$, HCl.

Scheme 10

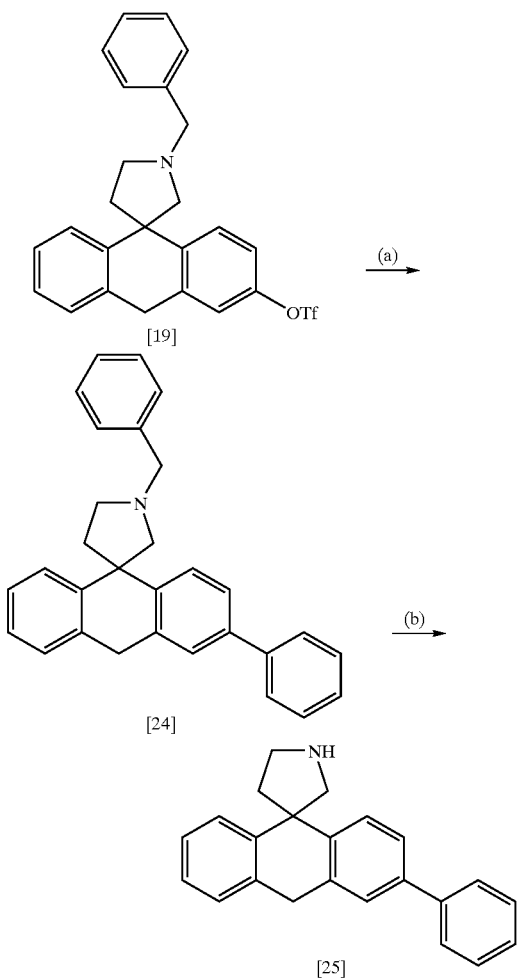

3-(3-Phenyl)-9,9-[spiro-3'-(n-benzyl)-pyrrolidinyl]-9,10-dihydroanthracene [24]

An oven dried flask equipped with a septum inlet and condenser was flushed with $N_2$ phenyl boronic acid (0.25 g, 2.043 mmol) 3-Trifluoromethane sulfonyl oxy-9,9-[spiro-3'-(n-benzyl)-pyrrolidinyl]-9,10-dihydroanthracene [19] (0.48 g, 0.980 mmol) and $K_2CO3$(0.282 g, 2.04 mmol) were added followed by anhydrous toluene (15 mL). $[(C_6H_5)_3P]_4Pd$ (0.035 g, 3 mol %) was added immediately and the reaction mixture was heated at 90° C. for 4 hr. The reaction mixture was then cooled to room temperature and diluted with EtOAc (25 mL) and washed with satd. NaHCO$_3$ soln., water, brine and dried (MgSO$_4$). The solvent was removed under reduced pressure to give a dark brown oil, which was purified by mplc using pet. ether as eluent to give 0.235 g (58%) of the product as a colorless oil. The oil was converted into its oxalate, mp. 138–139° C. (EtOAc—CH$_3$OH). $^1$H NMR (CDCl$_3$)d: 2.33–2.44 (m, 2H, CH$_2$),2.46–3.17 (m, 4H, CH$_2$), 3.75–3.78 (d, J=9 Hz, 2H, CH$_2$), 4.02–4.10 (m, 2H, CH$_2$), 7.12–7.84 (m, 17H, Ar—H). $^{13}$C NMR (CDCl$_3$)d: 35.92, 41.66, 49.79, 54.58 60.32, 67.02. Satisfactory elemental analyses could not be obtained.

3-(3-Phenyl)-9,9-[spiro-3'-pyrrolidinyl]-9,10-dihydroanthracene [25]

3-(3-Phenyl)-9,9-[spiro-3'-(n-benzyl)-pyrrolidinyl]-9,10-dihydroanthracene [24] (0.25 g, 0.622 mmol) was dissolved in CH$_3$OH (15 mL) and 10% Pd/C (0.10 g) was added under N$_2$. A few drops of HCl were added and the reaction mixture was hydrogenated on a parr-hydrogenator at 50 psi (4 days) and the catalyst was filtered off using celite. The filterate was evaporated and water (15 mL) was added and basified using 10% NaOH. The basic solution was extracted with CH$_2$Cl$_2$ (2×25 mL) and the combined extracts were washed with water, brine and dried (MgSO$_4$). The CH$_2$Cl$_2$ was removed under reduced pressure to give a yellow oil which was purified by mplc using CH$_2$Cl$_2$:CH$_3$OH (9:1) as eluent to give 0.081 g (42%) of the product as a colorless oil which darkened rapidly. The oil was converted into its fumarate salt, mp. 129–130° C. (EtOAc—CH$_3$OH). $^1$H NMR (DMSO-d$_6$)d: 2.35–2.39 (t, J=6Hz, 2H, CH$_2$), 3.33–3.3 (t, J=6 Hz, 2H, CH$_2$), 3.78 (s, 2H, CH$_2$), 4.02–4.04 (d, J=6 Hz, 2H, CH$_2$), 6.51 (s, 2H, CH=CH), 7.27–7.71 (m, 12H, Ar—H). $^{13}$C NMR (CDCl$_3$)d: 35.92, 46.92, 51.71, 58.88, 123.83, 126.26, 126.87, 127.54, 128.56, 135.99, 136.83, 138.86, 140.55, 141.22, 141.90. Anal. Calcd. For (C$_{23}$H$_{21}$N.C$_4$H$_4$O$_4$.H$_2$O): C, 72.16; H, 6.22; N, 3.08. Found. C, 71.62; H, 6.19; N, 2.84.

Example 11

Synthesis of Spiro[xanthenyl]-9,3'-pyrrolidine [30]

Compound [30] was synthesized as depicted in Scheme 11 and as described below. Referring to Scheme 11, reagents and conditions were as follows: (a) POCl$_3$, reflux, 45 min, (b) n-BuLi, BrCH$_2$COOC$_2$H$_5$, Et$_2$O, reflux, (c) 10% Pd/C, CH$_3$OH, HCl, (d) Borane-THF/THF; 6.0M HCl.

Scheme 11.

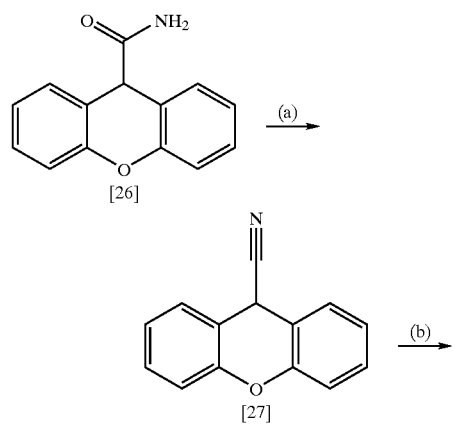

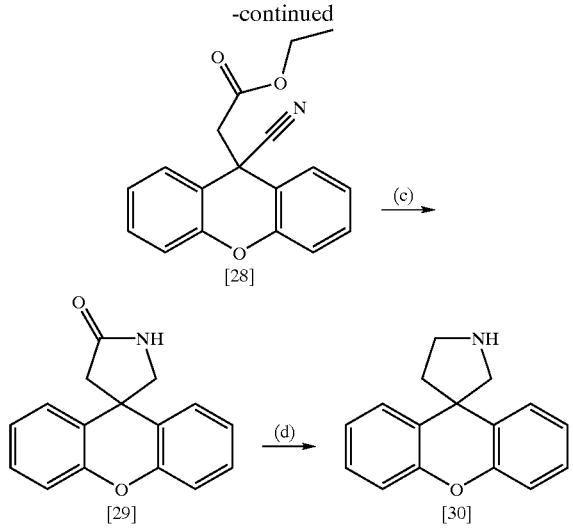

9H-Xanthene-9-carbonitrile [27]

POCl$_3$ (25 mL) was added to crystalline 9H-Xanthene-9-carboxamide [26] (1.5 g, 6.65 mmol) while stirring. The solution was then heated at reflux (45 min), when TLC showed complete absence of starting material. The solution was then poured into a mixture of crushed ice and NH$_4$OH with vigorous stirring. The solution was stirred (15 min) and excess of NH$_4$OH was added to keep the solution alkaline. The solid formed was extracted with ether (3×50 ml). The combined ether extracts were washed with water and brine, dried (MgSO$_4$) and evaporated under reduced pressure to give an yellow oil which crystallized immediately. The product was purified by mplc using pet. ether: acetone (8:2) as eluent to give 1.2 g (87%) 9H-Xanthene-9-carbonitrile as colorless needles, mp 97–98° C. (EtOH).

(9-Cyano-9H-xanthen-9-yl)-acetic acid ethyl ester [28]

9H-Xanthene-9-carbonitrile [27] (1.0 g, 4.825 mmol) was dissolved in anhydrous Et$_2$O and cooled in an icebath. n-Butyl lithium (1.93 mL, 6.75 mmol. 2.5M soln. in hexanes) was added dropwise over 10 min. with continuos stirring. Stirring was continued for 30 min. at the same temperature and then brought to room temperature. The reaction mixture was heated at reflux (1 hr), cooled in an icebath and ethyl bromo acetate (0.75 mL, 6.755 mmol) was added dropwise via syringe. The resulting mixture was heated at reflux (4 h) cooled and filtered. The residue was washed with ether (25 mL). Water (25 mL) was added to the filtrate and the organic layer was separated. The aqueous layer was once again extracted with ether (25 mL). The combined ether extracts were washed with water and brine, dried (MgSO$_4$) and evaporated under reduced pressure to give an oil which was purified by mplc using pet. ether: EtOAc (9:1) as eluent to give 0.9 g (64%) of the product as a colorless oil. $^1$H NMR (CDCl$_3$)d: 1.04–1.08 (t, J=7.5 Hz, CH$_3$), 3.01 (s, 2H, CH$_2$), 3.90–3.99 (q, 2H, CH$_2$), 7.14–7.69 (m, 8H, Ar—H). $^{13}$C NMR (CDCl$_3$)d: 13.54, 39.06, 48.47, 60.85, 116.88, 118.90, 119.75, 123.81, 127.34, 129.83, 150.30, 166.98.

Spiro[xanthenyl]-9,4'-pyrrolidin-2'-one [29]

A mixture of (9-Cyano-9H-xanthen-9-yl)-acetic acid ethyl ester [28] (0.50 g, 1.70 mmol), 10% Pd/C (0.15 g) in methanol (40 mL) and HCl (1 mL) was hydrogenated at 50 kg/cm$^3$ (3 days). The catalyst was filtered off with celite and the solvent was evaporated under reduced pressure to give a white semisolid. Water (25 mL) was added and the solution was made basic with 10% NaOH and extracted with EtOAc (3×25 mL). The combined EtOAc extracts were washed with water and brine, dried (MgSO$_4$) and evaporated under reduced pressure to give a colorless oil which crystallized immediately on standing. The solid was recrystallized from CHCl$_3$-pet.ether to give 0.295 g (69%) of the pure amide as a colorless needles, mp 182–183° C. $^1$H NMR (CDCl$_3$)d: 3.02 (s, 2H, CH$_2$), 3.82 (s, 2H, CH$_2$), 6.51 (s, 1H, NH), 7.07–7.44 (m, 8H, Ar—H). $^{13}$C NMR (CDCl$_3$)d: 39.98, 48.50, 60.72, 116.39, 123.70, 125.77, 126.46, 128.31, 149.59, 176.10.

Spiro[xanthenyl]-9,3'-pyrrolidine [30]

A 1.0M solution of BH$_3$-THF complex (5.0 ml, 5 mmol) was added at 0° C. to a well stirred solution of Spiro [xanthenyl]-9,4'-pyrrolidin-2'-one [29] (0.25 g, 0.99 mmol) in anhydrous THF (2 mL). The solution was brought to RT and then heated at reflux (8 h), cooled to RT and 6M solution of HCl (4 mL) was added cautiously to the reaction mixture. The reaction mixture was then heated at reflux (1 hr), cooled to RT and the solvent was removed under reduced pressure, resulting in a white suspension. Water (20 mL) was added to it and extracted with EtOAc (20 mL). The aqueous phase was then basified using 10% NaOH and extracted with Et$_2$O (3×25 ml). The combined Et$_2$O extracts were washed with water and brine, dried (MgSO$_4$) and the solvent was removed under reduced pressure to give 0.185 g (79%) the amine as colorless oil. The oil started to darken rapidly and was dissolved in anhydrous acetone and fumaric acid (0.15 g, 1.31 mmol) was added and heated. The solution on cooling gave the fumarate as pale pink powder, which remained on two recrystallizations. mp. 183–184° C. (EtOAc). $^1$H NMR (DMSO-d$_6$)d: 2.26–2.31 (t, J=9 Hz, 2H, CH$_2$), 3.41–3.45 (t, J=6 Hz, 2H, CH$_2$), 3.64 (s, 2H, CH$_2$), 6.54 (s, 2H, CH=CH), 7.11–7.64 (m, 8H, Ar—H). $^{13}$C NMR (DMSO-d$_6$)d: 44.35, 59.51, 115.96, 123.73, 126.54, 127.24, 128.22, 134.87, 140.12, 141.02, 149.87, 167.74, 179.90, 186.56. Anal. Calcd. For (C$_{17}$H$_{17}$N.C$_4$H$_4$O$_4$.0.5H$_2$O): C, 66.28;H, 5.56; N, 3.86. Found. C, 66.41; H, 5.59; N, 3.82

Example 12

Synthesis of Spiro[thioxanthenyl]-9,3'-pyrrolidine [36] Compound [36] was synthesized as depicted in Scheme 12, and as described below. Referring to Scheme 12, reagents and conditions were as follows: (a) NaBH$_4$, CH$_3$OH (b) (i) SOCl$_2$/Et$_2$O (ii) CuCN/C$_6$H$_6$ (c) n-BuLi, BrCH$_2$COOC$_2$H$_5$, Et$_2$O, reflux, (c) 10% Pd/C, CH$_3$OH, HCl, (d) Borane-THF/THF; 6.0M HCl.

Scheme 12

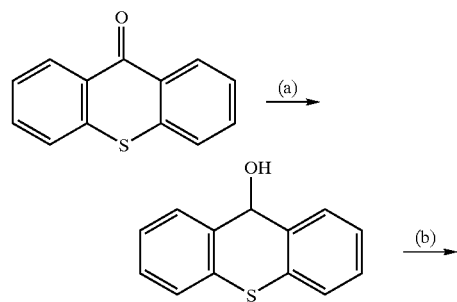

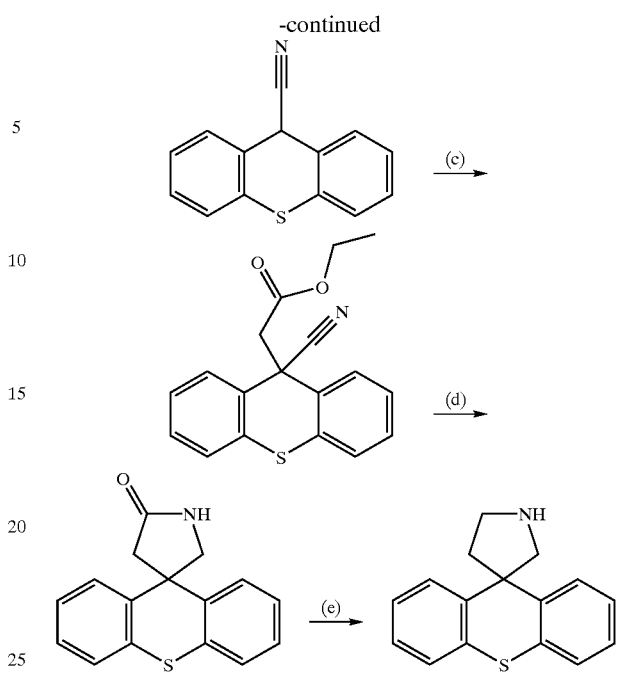

9H-Thioxanthen-9-ol [32]

A suspension of thioxanthen-9-one [31] (2 g, 9.42 mmol) in anhydrous CH$_3$OH (30 mL) was stirred under N$_2$ and NaBH$_4$ (1.42 g, 37.68 mmol) was added slowly in portions over 15 min. After complete addition the reaction mixture was heated at reflux (3 hr.) and cooled to room temperature. Ice-water was added and the reaction mixture was extracted with CH$_2$Cl$_2$ (3×50 mL). The combined CH$_2$Cl$_2$ extracts were washed with water, brine, dried (MgSO$_4$). The solvent was removed under reduced pressure to give a yellow solid, which was recrystallized from pet.ether to give 1.87 g (93%) of the alcohol as pale yellow needles, mp 104–105° C.

9H-Thioxanthene-9-carbonitrile [33]

A suspension of 9H-Thioxanthen-9-ol [32] (2.14 g, 9.98 mmol) in anhydrous Et$_2$O (20 mL) under N$_2$ and SOCl$_2$ (0.8 mL, 11.48 mmol) was added with caution via syringe with stirring at 0–5° C. The alcohol dissolved before a white solid began to separate. After stirring (1 hr.) at room temperature, the solvent was removed under reduced pressure and C$_6$H$_6$ (10 mL) was added and solvent removed to dryness again. All manipulations were performed with rigorous exclusion of air. Anhydrous C$_6$H$_6$ (20 mL) and CuCN powder (1.79 g, 19.97 mmol) were added and the suspension was stirred at reflux (4 hr.).The reaction mixture was filtered while hot and the residue was washed with hot C$_6$H$_6$ (50 mL). The filterate was evaporated to give a crystalline residue containing thioxanthene and thioxanthen-9-one as well as the desired nitrile. One recrystallizations from hexane removed thioxanthene and one recrystallizations from 2-propanol removed most of the thioxanthen-9one to provide 1.3 g (59%) of the pure nitrile, mp. 97–98° C.

(9-Cyano-9H-thioxanthen-9-yl)-acetic acid ethyl ester [34]

9H-thioxanthene-9-carbonitrile [33] (1.20 g, 5.37 mmol) was dissolved in anhydrous Et$_2$O and cooled in an icebath. n-Butyl lithium (2.14 mL, 5.37 mmol, 2.5M soln. in hexanes) was added dropwise over 10 min. with continuous stirring. Stirring was continued for 30 min. at the same temperature and then brought to room temperature. The reaction mixture was heated at reflux (1 hr) cooled in an icebath and ethyl bromo acetate (0.83 mL, 7.52 mmol) was added dropwise via syringe. The resulting mixture was heated at reflux (4 h) cooled and filtered. The residue was washed with ether (25 mL). Water (25 mL) was added to the filterate and the organic layer was separated. The aqueous layer was once again extracted with ether (25 mL). The combined ether extracts were washed with water and brine, dried (MgSO$_4$) and evaporated under reduced pressure to give an oil which was purified by mplc using pet. ether: EtOAc (9:1) as eluent to give 0.97 g (59%) of the product as a colorless oil. $^1$H NMR (CDCl$_3$)d: 1.08–1.12 (t, J=6 Hz, CH$_3$), 3.08 (s, 2H, CH$_2$), 3.95–4.03 (q, 2H, CH$_2$), 7.31–8.00 (m, 8H, Ar—H). $^{13}$C NMR (CDCl$_3$)d: 38.49, 47.63, 60.76, 118.91, 127.00, 127.24, 127.80, 128.15, 130.73, 130.98, 167.66.

Spiro[xanthenyl]-9,4'-pyrrolidin-2'-one [35]

A mixture of(9-Cyano-9H-thioxanthen-9-yl)-acetic acid-ethyl ester [34] (0.50 g, 1.61 mmol), 10% Pd/C (0.15 g) in methanol (40 mL) and HCl (1 mL) was hydrogenated at 50 kg/cm$^3$ (3 days). The catalyst was filtered off with celite and the solvent was evaporated under reduced pressure to give a white semisolid. Water (25 mL) was added and the solution was made basic with 10% NaOH and extracted with EtOAc (3×25 mL). The combined EtOAc extracts were washed with water and brine, dried (MgSO$_4$) and evaporated under reduced pressure to give a colorless oil which crystallized immediately on standing. The solid was recrystallized from CHCl$_3$-pet.ether to give 0.32 g (74%) of the pure amide as a white solid, mp 178–179° C. $^1$H NMR (CDCl$_3$)d: 3.19 (s, 2H, CH$_2$), 3.73 (s, 2H, CH$_2$), 6.13 (bs, 1H, NH), 7.22–7.53 (m, 8H, Ar—H). $^{13}$C NMR (CDCl$_3$)d: 49.60, 53.15, 124.69, 126.68, 127.61, 133.32, 137.72, 176.06.

Spiro[thioxanthenyl]-9,3'-pyrrolidine [36]

A 1.0M solution of BH$_3$-THF complex (3.75 ml, 3.75 mmol) was added at 0° C. to a well stirred solution of spiro[thioxanthenyl]-9,4'-pyrrolidin-2'-one [35](0.2 g, 0.74 mmol) in anhydrous THF (2 mL). The solution was brought to RT and then heated at reflux (8 h), cooled to RT and 6 M solution of HCl (4 mL) was added cautiously to the reaction mixture. The reaction mixture was then heated at reflux (1 hr), cooled to RT and the solvent was removed under reduced pressure, resulting in a white suspension. Water (20 mL) was added to it and extracted with EtOAc (20 mL). The aqueous phase was then basified using 10% NaOH and extracted with Et$_2$O (3×25 ml). The combined Et$_2$O extracts were washed with water and brine, dried (MgSO$_4$) and the solvent was removed under reduced pressure to give 0.092 g (49%) the amine as colorless oil. The oil started to darken rapidly and was dissolved in anhydrous acetone and converted into its oxalate, mp. 169–170° C. (EtOAc). $^1$H NMR (DMSO-d$_6$)d: 2.74 (bs, 2H, CH$_2$), 3.39 (bs, 2H, CH$_2$), 3.79 (s, 2H, CH$_2$), 7.36 (bs, 4H, Ar—H), 7.65 (bs, 4H, Ar—H). $^{13}$C NMR (DMSO-d$_6$)d: 24.64, 50.02, 51.38, 124.83, 127.02, 133.32, 137.19, 163.90, 185.34. Anal. Calcd. For (C$_{16}$H$_{15}$NS.C$_2$H$_2$O$_4$.0.25H$_2$): C, 62.14; H, 5.07; N, 4.02. Found. C, 61.90; H, 4.92; N, 3.86

Example 13
Affinity of Compounds for 5-HT2A Serotonin Receptor

Binding assays were conducted in which the affinity of each of the compounds of interest for the 5-HT$_{2A}$ serotonin receptor was tested. Assays were conducted with the 5-HT$_{2A}$ receptor in buffer consisting of 50 mM Tris-Cl, 0.5 mM EDTA, 5 mM MgCl$_2$, pH=7.4. The 5-HT$_{2A}$ affinity determinations used $^3$H-ketanserin as the radioligand and spiperone (K$_d$=0.8 nM) as the reference compound.

Binding assays were also conducted in which the affinity of selected compounds of interest for the H$_1$ histamine receptor was tested. Assays were conducted with the H$_1$ receptor in buffer consisting of 50 mM Tris-Cl, 0.5 mM EDTA, pH=7.4. The H$_1$ determinations used $^3$H-pyrilamine as the radioligand with chlorpheniramine as the reference compound.

The results are given in Table 2.

TABLE 2

Affinity of Selected SPAN Derivatives for 5-HT$_{2A}$ and H$_1$ Receptors

| Compound | 5-HT$_{2A}$ Ki (nM) | H$_1$ Ki (nM) |
|---|---|---|
| 5 | 3.8 | 8.5 |
| 23 | 3.5 | — |
| 17 | 3.7 | 40 |
| 21 | 6 | 1600 |
| 19 | 9.2 | — |
| 25 | 18 | — |
| 6 | 46 | — |
| 7 | 220 | — |
| 22 | 998 | — |
| 16 | 1000 | 74 |
| 20 | 2030 | — |
| 18 | 330 | — |
| 12 | 68 | — |
| 30 | 40 | 51 |
| 36 | 5 | 6 |

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

REFERENCES

Bordwell, F. G., Hughes, D. L. 1983, *J. Org. Chem.* 48 (13) 2216–2222.

Glennon, R. A., Dukat, M., El-Bermawy, M, Law, H, de los Angeles, J, Teitler, M, King, A and Herrick-Davis, K. 1994. *J. Med. Chem.* 37:1929–1935.

Glennon, R A, Naiman, N A, Peirson, M E, Smith, J D, Ismaiel, A M, Titeler, M and Lyon, R A. 1989. *J. Med. Chem.*, 32:1921.

Roth, B L, Craigo, S C, Choudhary, A U, Monsma, F J, Shen, Y, Miltzer, H Y, Sibley, D R. 1994, *J. Pharm. Exp Ther.* 268: 1403.

Vaganova, T. A., Panteluva, E. V., Tananakin, A. P., Steingarts, V. D., Bilkis, I. I. 1994, *Tetrahedron* 50 (33) 10011–10020.

We claim:

1. A compound having the formula

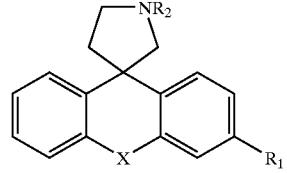

wherein
R1 and R2 are selected from the group consisting of —H, —OH, —OCH$_3$, halogen, aryl, alkylaryl, and substituted or unsubstituted branched or unbranched C$_1$–C$_{10}$ alkyl or alkylaryl, and may be the same or different, and X is selected from the group consisting of a) carbon with two —H substituents, b) carbon with one or two lower alkyl substituents, and c) —SO$_2$—;

2. The compound of claim 1 wherein R1 is selected from the group consisting of —H, —CH₂CH₂CH₂Ph, —OCH₃, —CH₂(CH₂)₄CH₃, phenyl, and —OH.

3. The compound of claim 1 wherein R2 is selected from the group consisting of —H, —CH₃ and CH₂Ph.

4. The compound of claim 1 wherein X is selected from the group consisting of —CH₂—, and —C(CH₃)₂—.

5. A compound having the formula

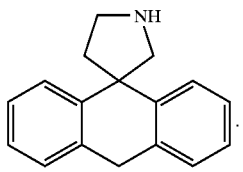

6. A compound having the formula

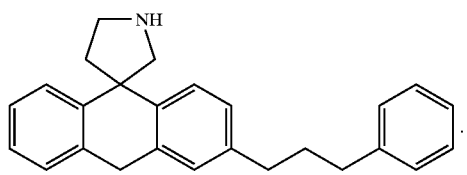

7. A compound having the formula

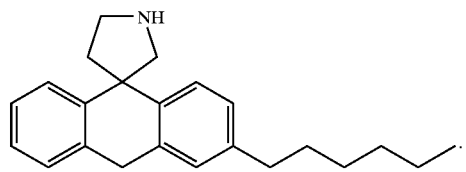

8. A compound having the formula

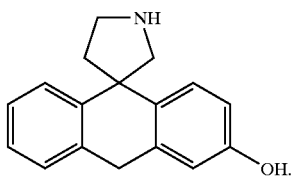

9. A compound having the formula

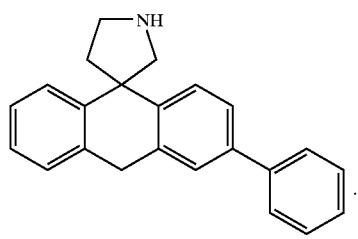

10. A compound having the formula

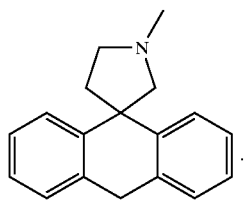

11. A compound having the formula

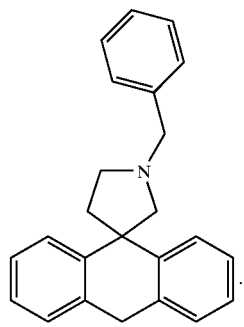

12. A compound having the formula

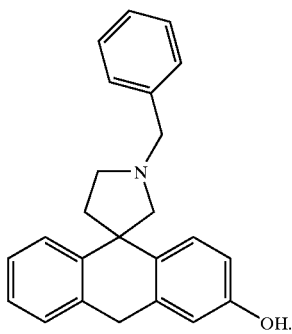

13. A compound having the formula

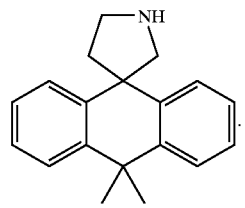

14. A pharmaceutical composition comprising, a compound of formula

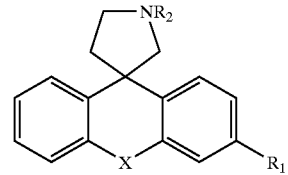

wherein

R1 and R2 are selected from the group consisting of —H, —OH, —OCH$_3$, halogen, aryl, alkylaryl, and substituted or unsubstituted branched or unbranched C$_1$–C$_{10}$ alkyl or alkylaryl, and may be the same or different, and X is selected from the group consisting of a) carbon with two —H substituents, b) carbon with one or two lower alkyl substituents, and c) —SO$_2$—, and a pharmaceutically acceptable carrier.

15. The pharmaceutical composition of claim 14 wherein R1 is selected from the group consisting of —H, —CH$_2$CH$_2$CH$_2$Ph, —OCH$_3$, —CH$_2$(CH$_2$)$_4$CH$_3$ and —OH.

16. The pharmaceutical composition of claim 14 wherein R2 is selected from the group consisting of —H, —CH$_3$ and CH$_2$Ph.

17. The pharmaceutical composition of claim 14 wherein X is selected from the group consisting of —CH$_2$—, and —C(CH$_3$)$_2$—.

18. A method of treating a condition caused by abnormal serotonin activity in a patient in need thereof, comprising the step of administering a compound of formula

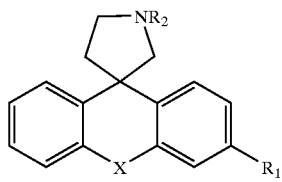

wherein

R1 and R2 are selected from the group consisting of —H, —OH, —OCH$_3$, halogen, aryl, alkylaryl, and substituted or unsubstituted branched or unbranched C$_1$–C$_{10}$ alkyl or alkylaryl, and may be the same or different, and X is selected from the group consisting of a) carbon with two —H substituents, b) carbon with one or two lower alkyl substituents, and c) —SO$_2$—, in a quantity to ameliorate symptoms of said condition in said patient; and wherein said condition is selected from the group consisting of depression, anxiety, schizophrenia, schizoaffective disorder, an eating disorder, and a sleep disorder.

19. The method of claim 18 wherein R1 is selected from the group consisting of —H, —CH$_2$CH$_2$CH$_2$Ph, —OCH$_3$, —CH$_2$(CH$_2$)$_4$CH$_3$ and —OH.

20. The method of claim 18 wherein R2 is selected from the group consisting of —H, —CH$_3$ and CH$_2$Ph.

21. The method of claim 18 wherein X is selected from the group consisting of —CH$_2$—, and —C(CH$_3$)$_2$—.

22. The method of claim 18 wherein said compound is an antagonist of 5HT$_2$ serotonin receptors.

23. The method of claim 18 wherein said compound is an antagonist of both 5HT$_2$ receptors and H1 receptors.

24. A method of blocking a 5HT$_2$ receptor in a patient in need thereof, comprising the step of identifying a patient that would benefit from blocking of the 5HT2 receptor, and administering to said patient a compound of formula

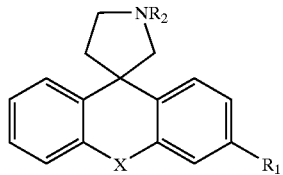

wherein

R1 and R2 are selected from the group consisting of —H, —OH, —OCH$_3$, halogen, aryl, alkylaryl, and substituted or unsubstituted branched or unbranched C$_1$–C$_{10}$ alkyl or alkylaryl, and may be the same or different, and X is selected from the group consisting of a) carbon with two —H substituents, b) carbon with one or two lower alkyl substituents, and c) a heteroatom or heteroatomic group selected from the group consisting of —O—; —S—; and —SO$_2$—, in a quantity to sufficient to block said 5HT$_2$ receptor, wherein said method is carried out to treat a condition selected from the group consisting of depression, anxiety, schizophrenia, schizoaffective disorder, an eating disorder, and a sleep disorder.

25. A method of blocking an H1 receptor in a patient in need thereof, comprising the step of identifying a patient that would benefit from blocking of the H1 receptor, and administering to said patient a compound of formula

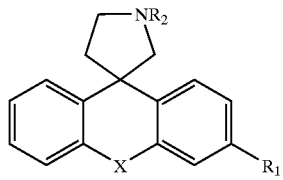

wherein

R1 and R2 are selected from the group consisting of —H, —OH, —OCH$_3$, halogen, aryl, alkylaryl, and substituted or unsubstituted branched or unbranched C$_1$–C$_{10}$ alkyl or alkylaryl, and may be the same or different, and X is selected from the group consisting of a) carbon with two —H substituents, b) carbon with one or two lower alkyl substituents, and c) a heteroatom or heteroatomic group selected from the group consisting of —O—; —S—; and —SO$_2$—, in a quantity to sufficient to block said 5HT$_2$ receptor, wherein said method is carried out to treat a condition selected from the group consisting of depression, anxiety, schizophrenia, schizoaffective disorder, an eating disorder, and a sleep disorder.

26. A method of blocking both a 5HT$_2$ receptor and an H1 receptor in a patient in need thereof, comprising the step of identifying a patient that would benefit from blocking of the 5HT$_2$ receptor and the H1 receptor, and administering to said patient a compound of formula

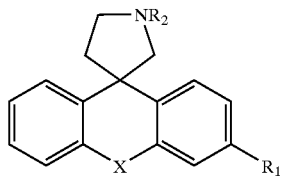

wherein

R1 and R2 are selected from the group consisting of —H, —OH, —OCH$_3$, halogen, aryl, alkylaryl, and substituted or unsubstituted branched or unbranched C$_1$–C$_{10}$alkyl or alkylaryl, and may be the same or different, and X is selected from the group consisting of a) carbon with two —H substituents, b) carbon with one or two lower alkyl substituents, and c) a heteroatom or heteroatomic group selected from the group consisting of —O—; —S—; and —SO$_2$—, in a quantity to sufficient to block said 5HT$_2$ receptor wherein method is carried out to treat a condition selected from the group consisting of depression, anxiety, schizophrenia, schizoaffective disorder, an eating disorder, and a sleep disorder.

27. A compound having the formula

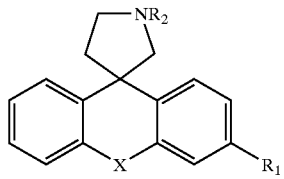

wherein

R1 is selected from the group consisting of —OH, —OCH$_3$, halogen, aryl, alkylaryl, and substituted or unsubstituted branched or unbranched C$_1$–C$_{10}$ alkyl or alkylaryl, and R2 is selected from the group consisting of —H, —OH, —OCH$_3$, halogen, aryl, alkylaryl, substituted or unsubstituted branched or unbranched C$_1$–C$_{10}$ alkyl, substituted or unsubstituted branched or unbranched C$_1$–C$_{10}$ alkylaryl and may be the same or different, and X is selected from the group consisting of a) carbon with two —H substituents, b) carbon with one or two lower alkyl substituents, and c) a heteroatom or heteroatomic group selected from the group consisting of —O—; —S—; and —SO$_2$—.

28. The compound of claim 27 wherein R1 is selected from the group consisting of —CH$_2$CH$_2$CH$_2$Ph, —OCH$_3$, —CH$_2$(CH$_2$)$_4$CH$_3$, phenyl, and —OH.

29. The compound of claim 27 wherein R2 is selected from the group consisting of —H, —CH$_3$ and CH$_2$Ph.

30. The compound of claim 27 wherein X is selected from the group consisting of —CH$_2$—, —C(CH$_3$)$_2$—, —O— and —S—.

31. A pharmaceutical composition comprising, a compound of formula

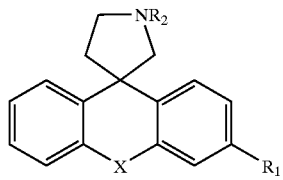

wherein

R1 is selected from the group consisting of —OH, —OCH$_3$, halogen, aryl, alkylaryl, and substituted or unsubstituted branched or unbranched C$_1$–C$_{10}$ alkyl or alkylaryl, and R2 is selected from the group consisting of —H, —OH, —OCH$_3$, halogen, aryl, alkylaryl, substituted or unsubstituted branched or unbranched C$_5$–C$_{10}$ alkyl, substituted or unsubstituted branched or unbranched C$_1$–C$_{10}$ alkylaryl and may be the same or different, and X is selected from the group consisting of a) carbon with two —H substituents, b) carbon with one or two lower alkyl substituents, and c) a heteroatom or heteroatomic group selected from the group consisting of —O—; —S—; and —SO$_2$—; and a pharmaceutically acceptable carrier.

32. The pharmaceutical composition of claim 31 wherein R1 is selected from the group consisting of —CH$_2$CH$_2$CH$_2$Ph, —OCH$_3$, —CH$_2$(CH$_2$)$_4$CH$_3$ and —OH.

33. The pharmaceutical composition of claim 31 wherein R2 is selected from the group consisting of —H, —CH$_3$ and CH$_2$Ph.

34. The pharmaceutical composition of claim 31 wherein X is selected from the group consisting of —CH$_2$—, and —C(CH$_3$)$_2$—, —O— and —S—.

35. A compound having the formula

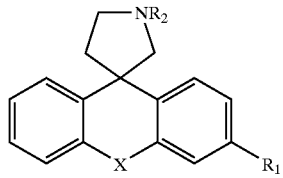

wherein

R1 is selected from the group consisting of —H, —OH, —OCH$_3$, halogen, aryl, alkylaryl, and substituted or unsubstituted branched or unbranched C$_1$–C$_{10}$ alkyl or alkylaryl, and R2 is selected from the group consisting of —OH, —OCH$_3$, halogen, aryl, alkylaryl, substituted or unsubstituted branched or unbranched C$_5$–C$_{10}$ alkyl, substituted or unsubstituted branched or unbranched C$_1$–C$_{10}$ alkylaryl and may be the same or different, and X is selected from the group consisting of a) carbon with two —H substituents, b) carbon with one or two lower alkyl substituents, and c) a heteroatom or heteroatomic group selected from the group consisting of —O—; —S—; and —SO$_2$—.

36. The compound of claim 35 wherein R1 is selected from the group consisting of —CH$_2$CH$_2$CH$_2$Ph, —OCH$_3$, —CH$_2$(CH$_2$)$_4$CH$_3$ phenyl, and —OH.

37. The compound of claim 35 wherein R2 is CH$_2$Ph.

38. The compound of claim 35 wherein X is selected from the group consisting of —CH$_2$—, and —C(CH$_3$)$_2$—, —O— and —S—.

39. A pharmaceutical composition comprising, a compound of formula

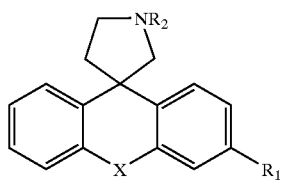

wherein
- R1 is selected from the group consisting of —H, —OH, —OCH$_3$, halogen, aryl, alkylaryl, and substituted or unsubstituted branched or unbranched C$_1$–C$_{10}$ alkyl or alkylaryl, and
- R2 is selected from the group consisting of —H, —OH, —OCH$_3$, halogen, aryl, alkylaryl, substituted or unsubstituted branched or unbranched C$_5$–C$_{10}$ alkyl, substituted or unsubstituted branched or unbranched C$_1$–C$_{10}$ alkylaryl and may be the same or different, and
- X is selected from the group consisting of a) carbon with two —H substituents, b) carbon with one or two lower alkyl substituents, and c) a heteroatom or heteroatomic group selected from the group consisting of —O—; —S—; and —SO$_2$—, and a pharmaceutically acceptable carrier.

40. The pharmaceutical composition of claim 39 wherein R1 is selected from the group consisting of —CH$_2$CH$_2$CH$_2$Ph, —OCH$_3$, —CH$_2$(CH$_2$)$_4$CH$_3$ and —OH.

41. The pharmaceutical composition of claim 39 wherein R2 is CH$_2$Ph.

42. The pharmaceutical composition of claim 39 wherein X is selected from the group consisting of —CH$_2$—, and —C(CH$_3$)$_2$—, —O— and —S—.

43. A compound having the formula

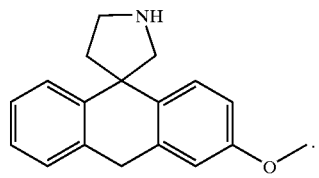

* * * * *